United States Patent
Lalena et al.

(10) Patent No.: US 8,827,554 B2
(45) Date of Patent: Sep. 9, 2014

(54) TUBE ALIGNMENT FOR MOBILE RADIOGRAPHY SYSTEM

(75) Inventors: Michael C. Lalena, Webster, NY (US); Joseph E. Stagnitto, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 219 days.

(21) Appl. No.: 13/083,860

(22) Filed: Apr. 11, 2011

(65) Prior Publication Data

US 2011/0249793 A1 Oct. 13, 2011

Related U.S. Application Data

(60) Provisional application No. 61/323,476, filed on Apr. 13, 2010, provisional application No. 61/449,932, filed on Mar. 7, 2011.

(51) Int. Cl.
*A61B 6/08* (2006.01)
*A61B 6/00* (2006.01)

(52) U.S. Cl.
CPC ............ *A61B 6/08* (2013.01); *A61B 6/4405* (2013.01); *A61B 6/4266* (2013.01); *A61B 6/461* (2013.01); *A61B 6/587* (2013.01); *A61B 6/542* (2013.01); *A61B 6/547* (2013.01); *A61B 6/4208* (2013.01)
USPC ......................................... 378/206; 378/98.5

(58) Field of Classification Search
USPC ................. 378/98.5, 205, 163, 206
See application file for complete search history.

(56) References Cited

U.S. PATENT DOCUMENTS

| | | | |
|---|---|---|---|
| 4,017,858 A | 4/1977 | Kuipers | |
| 4,246,486 A | 1/1981 | Madsen | |
| 4,752,948 A | 6/1988 | MacMahon | |
| 4,836,671 A | 6/1989 | Bautista | |
| 5,241,578 A | 8/1993 | MacMahon | |
| 5,388,143 A | 2/1995 | MacMahon | |
| 5,539,798 A | 7/1996 | Asahina et al. | |
| 5,550,889 A | 8/1996 | Gard et al. | |
| 5,617,462 A | 4/1997 | Spratt | |

(Continued)

FOREIGN PATENT DOCUMENTS

JP 2000-023955 1/2000

OTHER PUBLICATIONS

International Search Report & Written Opinion, International application No. PCT/US2011/032035, dated Dec. 19, 2011, 9 pages.

(Continued)

*Primary Examiner* — Hoon Song

(57) ABSTRACT

A radiography system for obtaining a radiographic image of a subject has a radiation source energizable to direct radiant energy along a radiation path and an imaging receiver sensitive to the radiant energy for forming the radiographic image. A sensor apparatus is disposed to provide one or more output signals that are indicative at least of centering of the radiation path with respect to the receiver, of an angle of the receiver relative to the radiation path, and of a source-to-image distance along the radiation path. A display apparatus generates, in response to the one or more output signals, a display that indicates the centering of the radiation path with respect to the receiver and that provides one or more values indicative of at least the source-to-image distance and the angle of the receiver relative to the radiation path.

20 Claims, 23 Drawing Sheets

(56) References Cited

U.S. PATENT DOCUMENTS

| | | | |
|---|---|---|---|
| 5,751,783 A | 5/1998 | Granfors et al. | |
| 5,949,811 A | 9/1999 | Baba et al. | |
| 6,047,042 A | 4/2000 | Khutoryansky et al. | |
| 6,154,522 A | 11/2000 | Cumings | |
| 6,192,105 B1 | 2/2001 | Hunter et al. | |
| 6,208,710 B1 | 3/2001 | Nagai | |
| 6,327,336 B1 | 12/2001 | Gingold et al. | |
| 6,404,851 B1 | 6/2002 | Possin et al. | |
| 6,422,750 B1 | 7/2002 | Kwasnick et al. | |
| 6,702,459 B2 | 3/2004 | Barnes et al. | |
| 6,760,405 B2 | 7/2004 | Ruetten et al. | |
| 6,895,268 B1 | 5/2005 | Rahn et al. | |
| 6,942,385 B2 | 9/2005 | Fadler et al. | |
| 6,944,266 B2 | 9/2005 | Yamazaki et al. | |
| 6,950,492 B2 | 9/2005 | Besson | |
| 7,010,091 B2 | 3/2006 | Hayashida et al. | |
| 7,120,229 B2 | 10/2006 | Takasawa | |
| 7,156,553 B2 | 1/2007 | Tanaka et al. | |
| 7,345,274 B2 | 3/2008 | Nilsson | |
| 7,368,724 B2 | 5/2008 | Morii et al. | |
| 7,490,986 B2 | 2/2009 | Takekoshi et al. | |
| 7,519,155 B2 | 4/2009 | Mollus et al. | |
| 7,581,884 B1 | 9/2009 | Barnes et al. | |
| 7,601,961 B2 | 10/2009 | Franklin et al. | |
| 7,613,276 B2 | 11/2009 | Sendai | |
| 7,632,016 B1 | 12/2009 | Huang et al. | |
| 7,744,279 B2 | 6/2010 | Heath et al. | |
| 7,780,350 B2 | 8/2010 | Tranchant et al. | |
| 7,794,144 B2 | 9/2010 | Windt | |
| 7,798,710 B1 | 9/2010 | Barnes et al. | |
| 2002/0150215 A1 | 10/2002 | Barnes et al. | |
| 2002/0188194 A1 | 12/2002 | Cosman | |
| 2003/0165216 A1 | 9/2003 | Walker et al. | |
| 2004/0101100 A1 | 5/2004 | Morii et al. | |
| 2004/0105526 A1* | 6/2004 | Zhang et al. | 378/205 |
| 2005/0058244 A1 | 3/2005 | Tanaka et al. | |
| 2005/0169425 A1 | 8/2005 | Takasawa | |
| 2006/0109958 A1 | 5/2006 | Ertel et al. | |
| 2006/0269114 A1 | 11/2006 | Metz | |
| 2007/0030957 A1* | 2/2007 | Pommi | 378/197 |
| 2007/0244388 A1 | 10/2007 | Sato et al. | |
| 2007/0255087 A1 | 11/2007 | Minai | |
| 2007/0297569 A1 | 12/2007 | Saunders | |
| 2008/0130837 A1 | 6/2008 | Heath et al. | |
| 2008/0198968 A1 | 8/2008 | Takekoshi et al. | |
| 2008/0204012 A1 | 8/2008 | Krueger et al. | |
| 2008/0240346 A1 | 10/2008 | Kashiwagi et al. | |
| 2009/0060145 A1 | 3/2009 | Tranchant et al. | |
| 2009/0086926 A1* | 4/2009 | Wang et al. | 378/206 |
| 2009/0136000 A1* | 5/2009 | Nishii et al. | 378/98.3 |
| 2009/0180590 A1 | 7/2009 | Borgmann et al. | |
| 2009/0257561 A1* | 10/2009 | Okuno et al. | 378/116 |
| 2010/0002831 A1 | 1/2010 | Maack | |

OTHER PUBLICATIONS

International Search Report & Written Opinion, International application No. PCT/US2011/032020, date Nov. 22, 2011, 8 pages.
One-page brochure for EasyPos dental x-ray positioning system from website, Mar. 2010. hyphendev.fr file PubEasypos08v3.pdf.
International Search Report, International application No. PCT/US2012/0262212, dated Aug. 30, 2012, 2 pages.
Supplementary European Search Report completed Mar. 5, 2014 for European Patent Application No. 11 76 9395.2, 2 pages.
Supplementary Partial European Search Report completed Apr. 29, 2014 for European Patent Application No. 11 76 9406, 1 page.

* cited by examiner

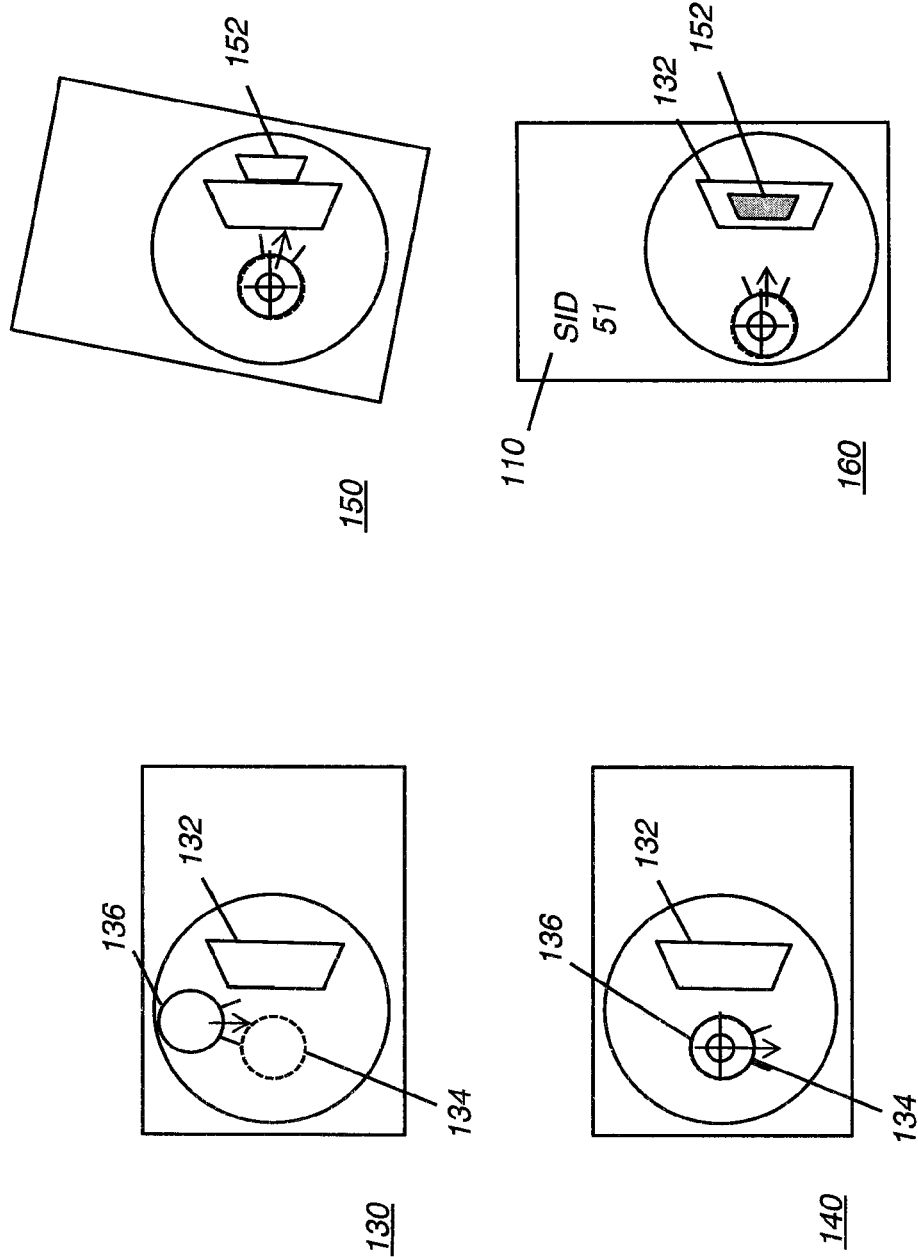

TUBE ALIGNMENT FOR MOBILE RADIOGRAPHY SYSTEM

CROSS REFERENCE TO RELATED APPLICATION

This is a 35 U.S.C 111a application that claims the benefit of U.S. Provisional Application Ser. No. 61/323,476, filed 13 Apr. 2010, entitled "MOBILE UNIT HAVING TUBE ALIGNMENT SYSTEM," by Michael C. Lalena and of U.S. Provisional Application Ser. No. 61/449,932, filed 7 Mar. 2011, entitled "GRAPHIC USER INTERFACE FOR MOBILE UNIT" by Joseph Stagnitto et al.

FIELD OF THE INVENTION

The invention relates generally to the field of radiographic imaging, and in particular to alignment apparatus in radiographic imaging systems. More specifically, the invention relates to methods and apparatus for assisting in alignment of the x-ray source to the imaging receiver and grid.

BACKGROUND OF THE INVENTION

When an x-ray image is obtained, there is generally an optimal distance and angle between the radiation source and the two dimensional receiver that records the image data. In most cases, it is preferred that the x-ray source provide radiation in a direction that is perpendicular to the surface of the recording medium. For this reason, large-scale radiography systems mount the radiation head and the recording medium holder at a specific angle relative to each other. Orienting the head and the receiver typically requires a mounting arm of substantial size, extending outward well beyond the full distance between these two components. With such large-scale systems, source-to-image distance (SID) is tightly controlled and unwanted tilt or skew of the receiver is thus prevented by the hardware of the imaging system itself. Further, because the spatial positioning and geometry of conventional large-scale systems is well-controlled, proper use and alignment of a grid, positioned in front of the imaging receiver, is straightforward.

Mobile x-ray apparatus are of particular value in intensive care unit (ICU) and other environments where timely acquisition of a radiographic image is important. Because it can be wheeled around the ICU or other area and brought directly to the patient's bedside, a mobile x-ray apparatus allows an attending physician or clinician to have recent information on the condition of a patient and helps to reduce the risks entailed in moving patients to stationary equipment in the radiological facility.

The perspective view of FIG. 1 shows an example of a conventional mobile x-ray apparatus that can be employed for computed radiography (CR) and/or digital radiography (DR). A mobile radiography unit 600 has a frame 620 that includes a display 610 for display of obtained images and related data and a control panel 612 that allows functions such as storing, transmitting, modifying, and printing of the obtained image.

For mobility, unit 600 has one or more wheels 615 and one or more handle grips 625, typically provided at waist-, arm-, or hand-level, that help to guide unit 600 to its intended location. A self-contained battery pack typically provides source power, eliminating the need for operation near a power outlet.

Mounted to frame 620 is a support member 635 that supports an x-ray source 640, also termed an x-ray tube or tube head, mounted on a boom apparatus 70, more simply termed a boom 70. A generator may also be mounted adjacent the tube head or, alternately, within frame 620. In the embodiment shown, support member 635 has a vertical column 64 of fixed height. Boom 70 extends outward a variable distance from support member 635 and rides up and down column 64 to the desired height for obtaining the image. Boom 70 may extend outward by a fixed distance or may be extendible over a variable distance. Height settings for the x-ray source 640 can range from low height for imaging feet and lower extremities to shoulder height and above for imaging the upper body portions of patients in various positions. In other conventional embodiments, the support member for the x-ray source is not a fixed column, but is rather an articulated member that bends at a joint mechanism to allow movement of the x-ray source over a range of vertical and horizontal positions.

With the advent of portable radiation imaging apparatus, such as those used in Intensive Care Unit (ICU) environments, a fixed angular relationship between the radiation source and two-dimensional radiation receiver and any accompanying grid is no longer imposed by the mounting hardware of the system itself. Instead, an operator is required to aim the radiation source toward the receiver surface, providing as perpendicular an orientation as possible, typically using a visual assessment. In computed radiography (CR) systems, the two-dimensional image-sensing device itself is a portable cassette that stores the readable imaging medium. In direct digital radiography (DR) systems, the two-dimensional image-sensing receiver is a digital detector with either flat, rigid, or flexible substrate support.

The receiver itself, however, may not be visible to the technician once it is positioned behind the patient. This complicates the alignment task for portable systems, requiring some method for measuring SID, tilt angle, and centering, and making it more difficult to use a grid effectively for reducing the effects of scatter. Because of this added complexity with a portable radiography system, the technician may choose not to use a grid; the result without a grid, however, is typically a lower-quality image.

There have been a number of approaches to the problem of providing methods and tools to assist operator adjustment of x-ray source-to-receiver angle. One conventional approach has been to provide mechanical alignment in a more compact fashion, such as that described in U.S. Pat. No. 4,752,948 entitled "Mobile Radiography Alignment Device" to MacMahon. A platform is provided with a pivotable standard for maintaining alignment between an imaging cassette and radiation source. However, complex mechanical solutions of this type tend to reduce the overall flexibility and portability of these x-ray systems. Another type of approach, such as that proposed in U.S. Pat. No. 6,422,750 entitled "Digital X-ray Imager Alignment Method" to Kwasnick et al. uses an initial low-exposure pulse for detecting the alignment grid; however, this method would not be suitable for portable imaging conditions where the receiver must be aligned after it is fitted behind the patient.

Other approaches project a light beam from the radiation source to the receiver in order to achieve alignment between the two. Examples of this approach include U.S. Pat. No. 5,388,143 entitled "Alignment Method for Radiography and Radiography Apparatus Incorporating Same" and No. 5,241,578 entitled "Optical Grid Alignment System for Portable Radiography and Portable Radiography Apparatus Incorporating Same", both to MacMahon. Similarly, U.S. Pat. No. 6,154,522 entitled "Method, System and Apparatus for Aiming a Device Emitting Radiant Beam" to Cumings describes the use of a reflected laser beam for alignment of the radiation target. However, the solutions that have been presented using light to align the film or CR cassette or DR receiver are constrained by a number of factors. The '143 and '578 MacMahon disclosures require that a fixed Source-to-Image Distance (SID) be determined beforehand, then apply triangulation with this fixed SID value. Changing the SID requires a number of adjustments to the triangulation settings. This arrangement is less than desirable for portable imaging systems that allow a variable SID. Devices using lasers, such as that described in the '522 Cumings disclosure, in some cases can require much more precision in making adjustments than is necessary.

Other examples in which light is projected from the radiation source onto the receiver are given in U.S. Pat. No. 4,836,671 entitled "Locating Device" to Bautista and U.S. Pat. No. 4,246,486 entitled "X-ray Photography Device" to Madsen. Both the Bautista '671 and Madsen '486 approaches use multiple light sources that are projected from the radiation source and intersect in various ways on the receiver.

Significantly, the solutions noted above are often of little of no value where the receiver and its accompanying grid are hidden from view, lying fully behind the patient as may be the case, for example, for chest x-ray imaging with a portable system. Today's portable radiation imaging devices allow considerable flexibility for placement of the film cassette, CR cassette, or Digital Radiography DR receiver by the radiology technician. The patient need not be in a horizontal position for imaging, but may be at any angle, depending on the type of image that is needed and on the ability to move the patient for the x-ray examination. The technician can manually adjust the position of both the cassette or receiver and the radiation source independently for each imaging session. Thus, it can be appreciated that an alignment apparatus for obtaining the desired angle between the radiation source and the grid and image receiver must be able to adapt to whatever orientation is best suited for obtaining the image. Tilt sensing, as has been conventionally applied and as is used in the device described in U.S. Pat. No. 7,156,553 entitled "Portable Radiation Imaging System and a Radiation Image Detection Device Equipped with an Angular Signal Output Means" to Tanaka et al. and elsewhere, does not provide sufficient information on cassette-to-radiation source orientation, except in the single case where the cassette lies level. More complex position sensing devices can be used, but can be subject to sampling and accumulated rounding errors that can grow worse over time, requiring frequent resynchronization.

Thus, it is apparent that conventional alignment solutions may be workable for specific types of systems and environments; however, considerable room for improvement remains. Portable radiography apparatus must be compact and lightweight, which makes the mechanical alignment approach such as that given in the '948 MacMahon disclosure less than desirable. The constraint to direct line-of-sight alignment reduces the applicability of many types of reflected light based methods to a limited range of imaging situations. The complex sensor and motion control interaction required by the Tanaka et al. '553 solution would add considerable expense, complexity, weight, and size to existing designs, with limited benefits. Many less expensive portable radiation imaging units do not have the control logic and motion coordination components that are needed in order to achieve the necessary adjustment. None of these approaches gives the operator the needed information for making a manual adjustment that is in the right direction for correcting misalignment, particularly where a grid is used.

Yet another problem not addressed by many of the above solutions relates to the actual working practices of radiologists and radiological technicians. A requirement for perpendicular delivery of radiation, given particular emphasis in the Tanaka et al. '553 application, is not used in all cases because it is not optimal for all types of imaging. In fact, there are some types of diagnostic images for which an oblique (nonperpendicular) incident radiation angle is most desirable, provided that the grid alignment is acceptable for the given angle. For example, for the standard chest anterior-posterior (AP) view, the recommended central ray angle is oblique from the perpendicular (normal) by approximately 3-5 degrees. Conventional alignment systems, while they provide for normal incidence of the central ray, do not adapt to assist the technician for adjusting to an oblique angle.

Still other problems relate to the need to achieve a source-to-image distance (SID) that is well-suited for the image to be obtained and for the grid used. Conventional alignment solutions do not provide SID information, leaving it to the technician to make separate measurements or to make an approximate SID adjustment. Moreover, conventional solutions do not provide the technician with tools to help reduce backscatter, caused by misalignment or poor adjustment of the collimator blades. This type of scatter, while not particularly problematic with other types of radiographic imaging, such as dental and mammographic imaging, can be troublesome with portable radiographic imaging apparatus, since the radiation is directed over a broad area. Radiation that works past the imaging receiver and any blocking element associated with the receiver can inadvertently be reflected back into the receiver, adversely affecting image quality. To reduce backscatter as much as possible for chest x-rays and other types of x-ray, the technician is required to estimate the location and orientation or outline of the imaging receiver and to adjust the collimator accordingly.

Thus, it can be seen that there is a need for an apparatus that enables proper angular alignment and centering of a radiation source relative to an image receiver for recording a radiation image.

SUMMARY OF THE INVENTION

An object of the present invention is to advance the art of radiographic imaging by providing apparatus and methods to aid in alignment and proper positioning of the radiation source to a radiation receiver. A related object of the present invention is to provide a display that indicates the location and outline of the radiation receiver relative to the path of the x-ray beam, as well as source-to-image distance and angular orientation of the receiver relative to the source. The display may appear on a display monitor or may be projected directly onto the patient.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there can be provided a radiography system for obtaining a radiographic image of a subject, the system comprising a radiation source energizable to direct radiant energy along a radiation path; an imaging receiver sensitive to the radiant energy for forming the radiographic image; a sensor apparatus that is disposed to provide one or more output signals that are indicative at least of centering of the radiation path with respect to the receiver, of an angle of the receiver relative to the radiation path, and of a source-to-image distance along the radiation path; and a display apparatus that generates, in response to the one or more output signals, a display that indicates the centering of the radiation path with respect to the receiver and that provides one or more values indicative of at least the source-to-image distance and the angle of the receiver relative to the radiation path.

According to one aspect of the invention, there can be provided a radiography system for obtaining a radiographic image of a subject, the system comprising a radiation source energizable to direct radiant energy along a radiation path; an imaging receiver sensitive to the radiant energy for forming the radiographic image as a digital image; a sensor apparatus that is disposed to provide one or more output signals that are indicative at least of an outline of the imaging receiver, of centering of the radiation path with respect to the receiver, of an angle of the receiver relative to the radiation path, and of a source-to-image distance along the radiation path; and a display apparatus that generates, in response to the one or more output signals, a display that indicates the outline of the imaging receiver and centering of the radiation path with respect to the receiver and displays one or more numeric values indicative of at least the source-to-image distance and the angle of the receiver relative to the radiation path.

According to one aspect of the invention, there can be provided a method for obtaining a radiographic image of a subject comprising obtaining one or more signals indicative of centering of an imaging receiver with respect to a radiation path from a radiation source, of an angle of the receiver relative to the radiation path, and of a source-to-image distance along the radiation path; and generating, in response to the one or more obtained signals, a display that shows at least the centering of the imaging receiver and displaying one or more values indicative of the source-to-image distance or the angle or both.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

FIG. 11 shows a sequence of operator interface display screens for a display screen that is mounted near the collimator that changes orientation as the radiation source angle changes.

DETAILED DESCRIPTION OF THE INVENTION

Figure 1:
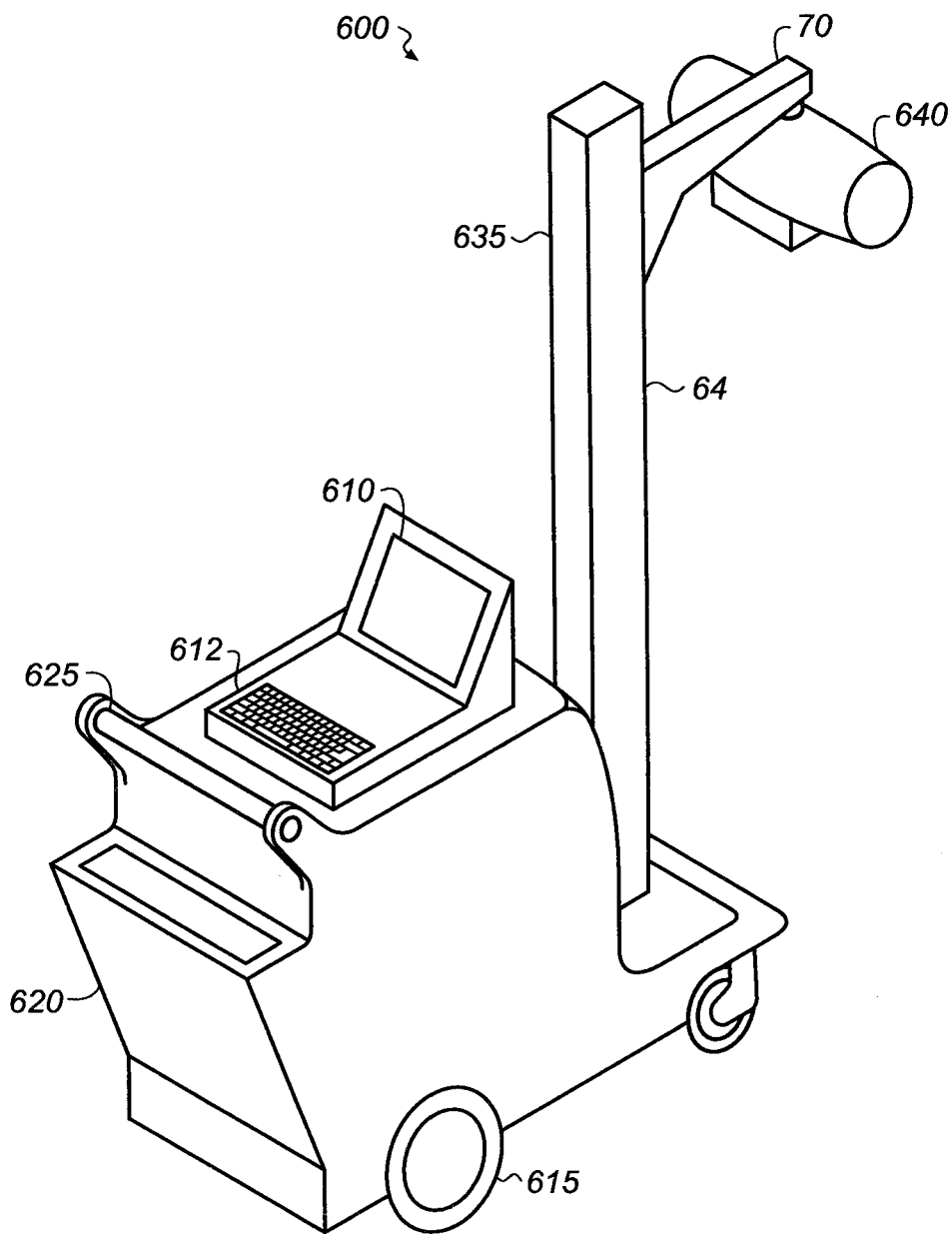
FIG. 1 shows a perspective view of one type of conventional mobile radiography unit.

The following is a detailed description of the preferred embodiments of the invention, reference being made to the drawings in which the same reference numerals identify the same elements of structure in each of the several figures.

In the context of the present disclosure, the term "imaging receiver", or more simply "receiver", may include a cassette that has a photostimulable medium, such as a film or phosphor medium, for example, or may include a detector array that records an image according to radiation emitted from the radiation source.

As used herein, the term "energizable" indicates a device or set of components that perform an indicated function upon receiving power and, optionally, upon receiving an enabling signal.

Figure 2A:
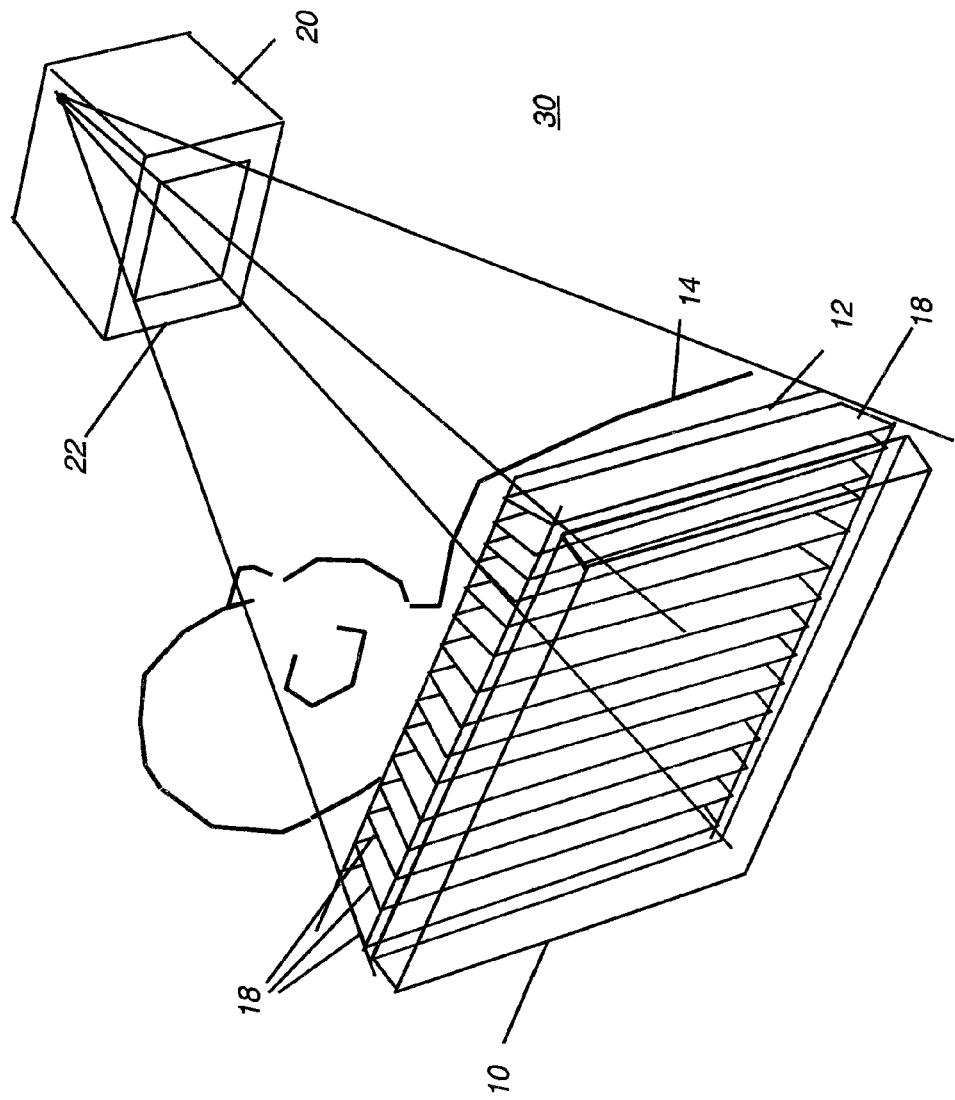
FIG. 2A is a perspective view showing the relative relationship of the patient being imaged to basic components of a diagnostic imaging apparatus.

The perspective view of FIG. 2A shows components of a radiographic imaging apparatus 30. A radiation source 20, such as an x-ray source, directs radiation toward a patient 14. A receiver 10 positioned behind the patient forms the diagnostic image from the incident radiation passing through patient 14. Receiver 10 may have a photostimulable medium, such as a film or phosphor medium, for example, or may have a detector array that records an image according to radiation emitted from radiation source 20. Receiver 10 may have landscape or portrait orientation. An optional antiscatter grid 12 has plates 18 arranged as shown in FIG. 1A, just above the surface of the receiver 10. Radiation source 20 has a collimator 22 that defines the radiation field that is directed outward from source 20, toward receiver 10 in the example of FIG. 2A.

Figure 2B:
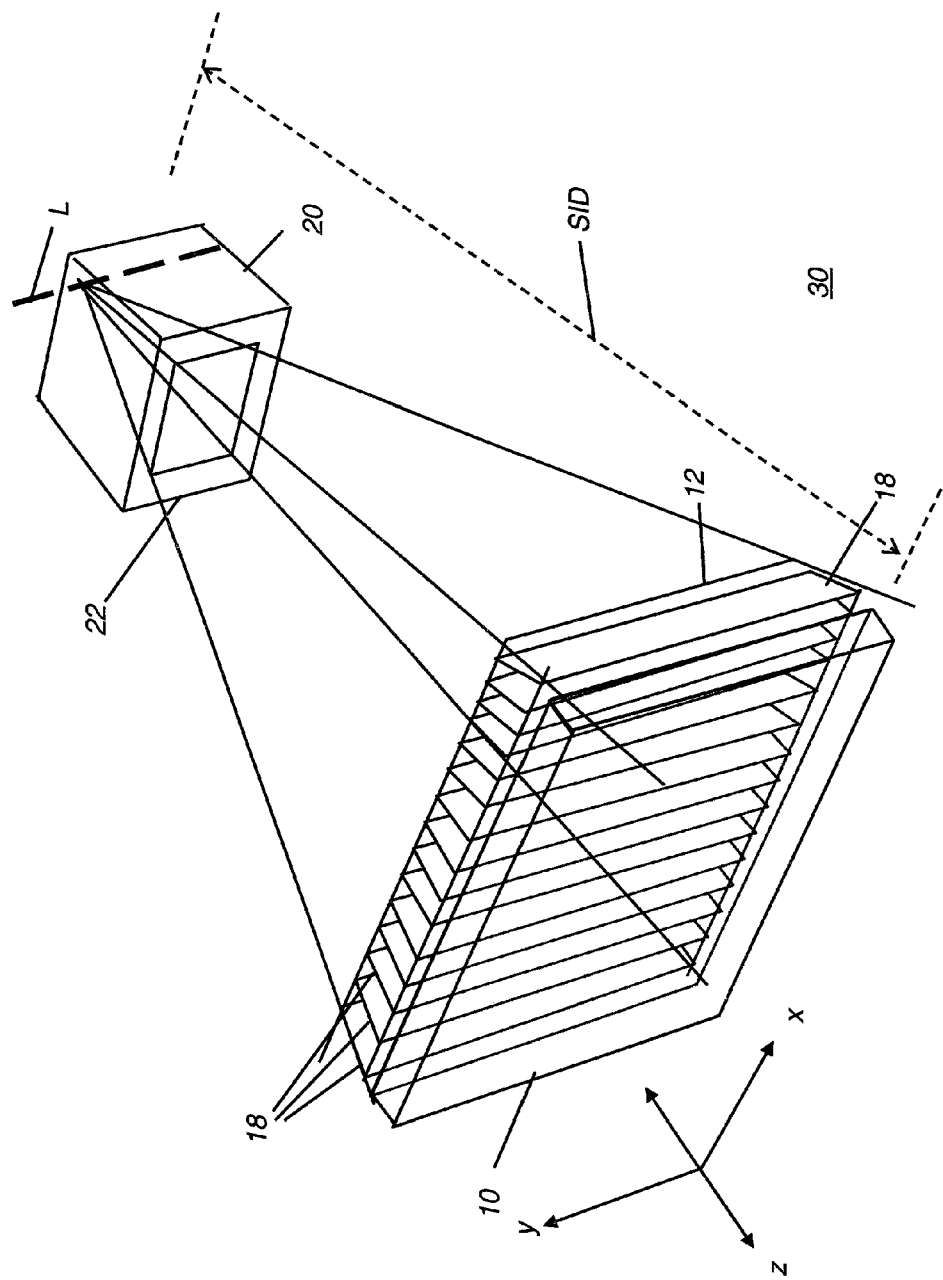
FIG. 2B is a perspective view showing important dimensional relationships for imaging system setup.

Radiation source 20 has an adjustable angular orientation for directing radiation toward receiver 10. FIG. 2B (with patient 14 not shown for better visibility of system components) shows coordinate xyz axes. Here, the source-to-image distance (SID) is in the general direction of the z axis. In FIG. 2B, radiation source 20 is in its aligned position, at a suitable SID from receiver 10. Grid plates 18 are angularly arranged so that they define a focal line L where their respective planes converge at the SID. For best alignment for most imaging in such an embodiment, radiation source 20 should be centered near focal line L and have the face portion of collimator 22 generally parallel to the planar surface of receiver 10. However, there can be image types for which a slight angular offset is preferred.

Figure 2C:
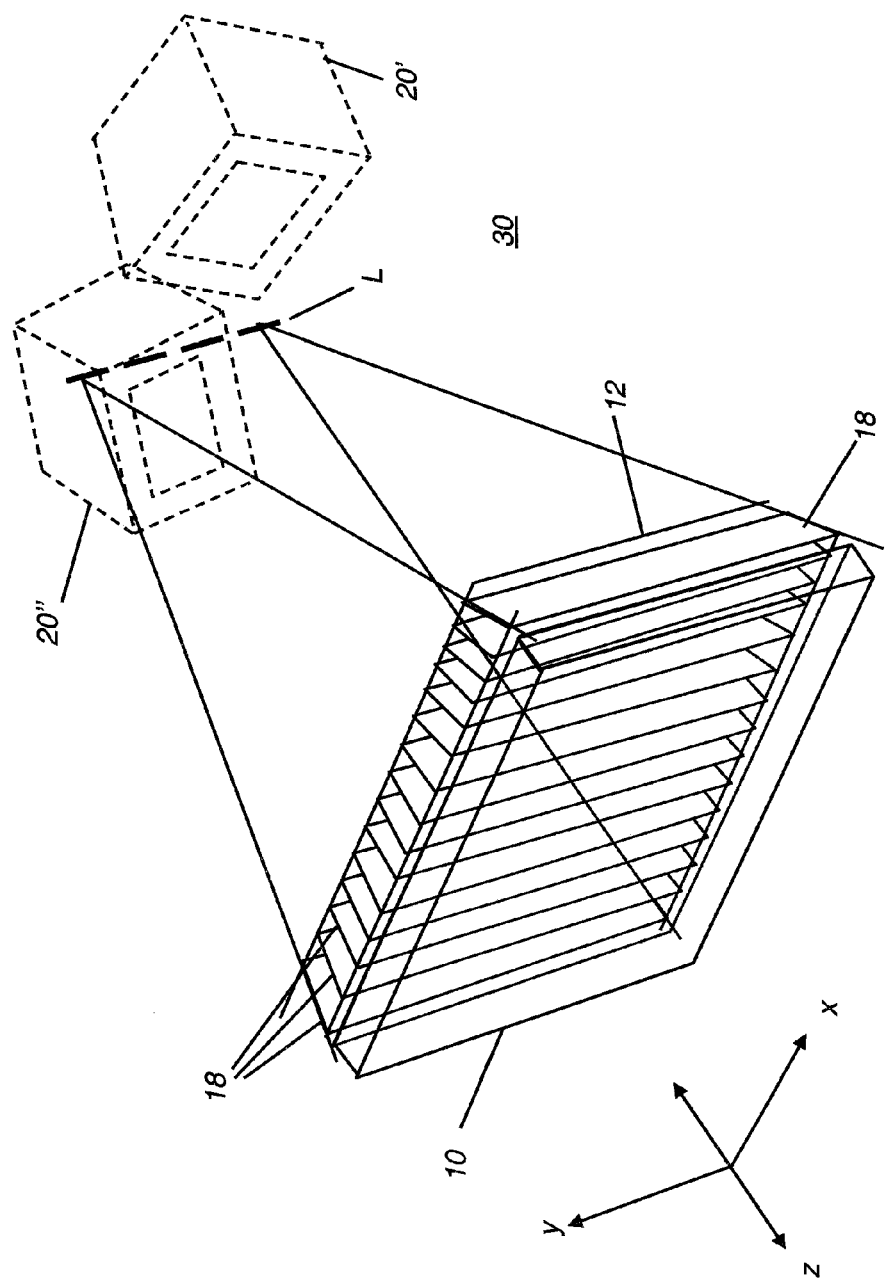
FIG. 2C is a perspective view showing exemplary out-of-alignment positioning.

FIG. 2C, by contrast, shows phantom outlines at 20' and 20" for poor positioning of radiation source 20. At positions 20' and 20" shown in phantom, the SID is almost acceptable; however, radiation source 20 is not centered near focal line L and its angular orientation is badly skewed. Alignment of the radiation source with the grid would be poor at these and similar out-of-alignment positions, degrading image quality or, at worst, preventing a suitable diagnostic image from being obtained.

Figure 3A:
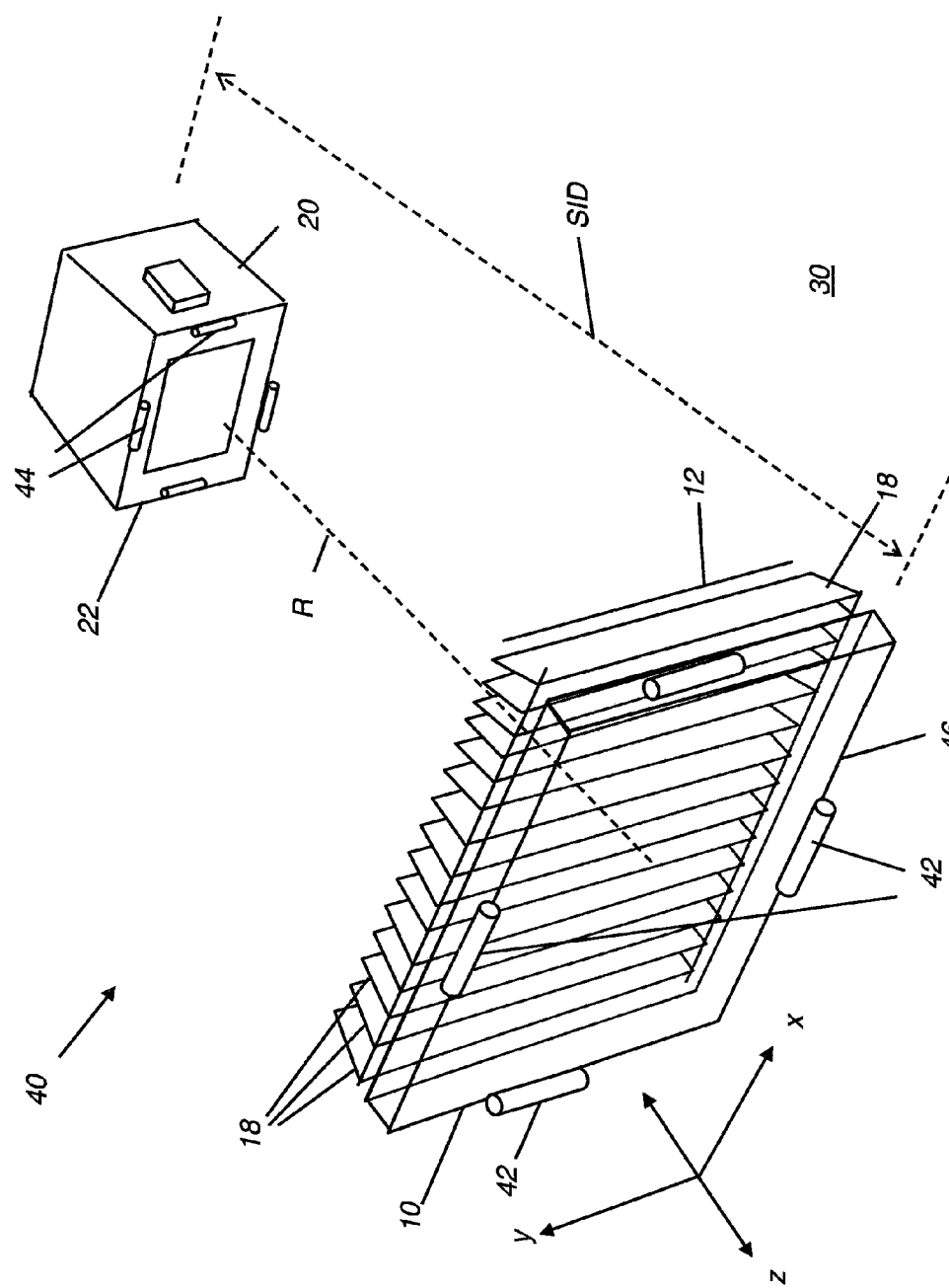
FIG. 3A is a perspective view showing the operation of one portion of an alignment apparatus in one embodiment.
Figure 3B:
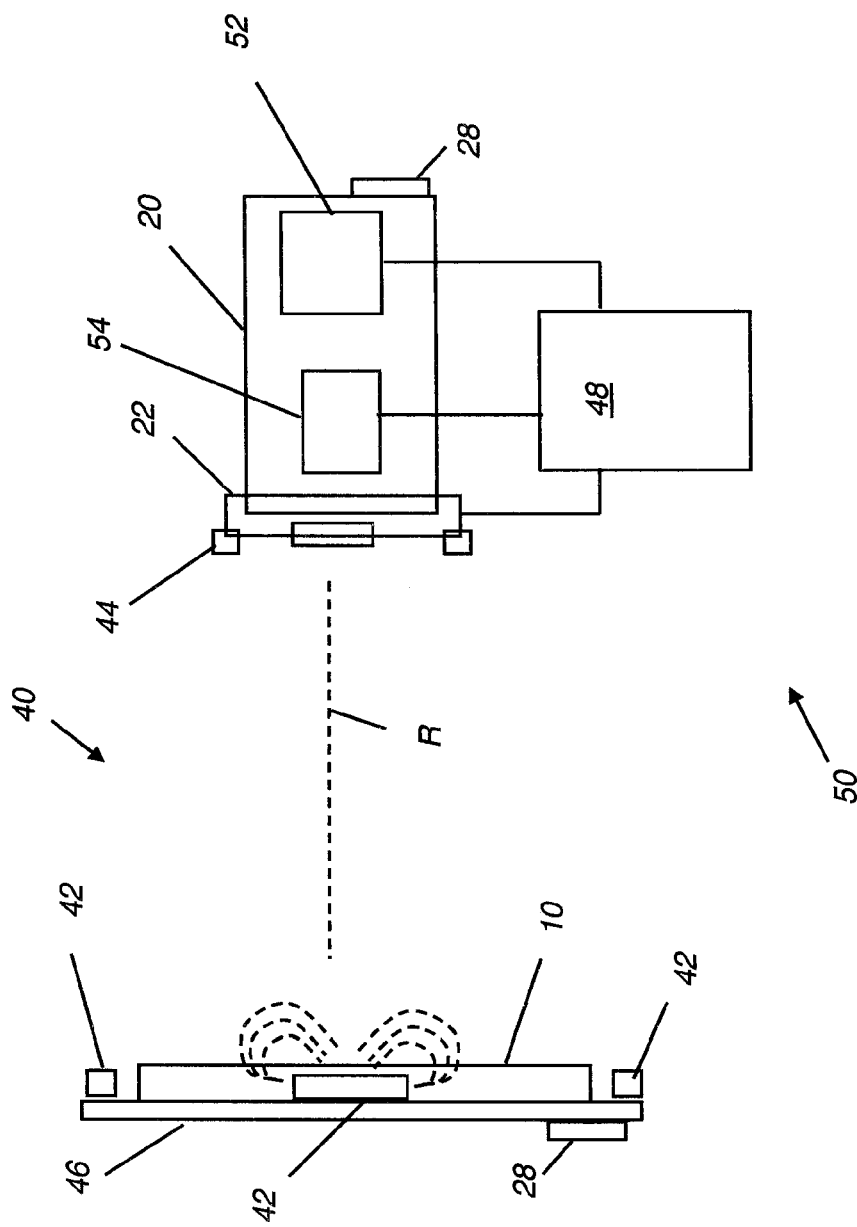
FIG. 3B is a side view block diagram that shows components used for achieving suitable tube to receiver/grid alignment according to an embodiment of the present invention.

The perspective view of FIG. 3A and side view of FIG. 3B show the use of a sensor apparatus 40 that is energizable to sense the relative spatial relationship between radiation source 20 having a radiation path represented as path R and distributed about a central axis and imaging receiver 10 sensitive to radiant energy and positioned adjacent the subject for forming the radiographic image and to generate one or more output signals indicative of the relative spatial relationship. In the embodiment shown in FIGS. 3A and 3B, a holder 46 has one or more electromagnetic coils 42 that generate an electromagnetic field or signal that is detected by one or more sensor elements 44, shown mounted near collimator 22. Holder 46 also holds receiver 10. In an alternate embodiment, sensor apparatus 40 components are built into receiver 10. In yet another alternate embodiment, signals are generated from one or more components on collimator 22 and detected by sensor elements on receiver 10. An additional inclinometer 28 or other device for obtaining an angular measurement can be provided on either or both receiver 10 or radiation source 20.

It can be appreciated by those skilled in the position-sensing arts that there are a number of possible configurations that can be used as sensor apparatus 40 for position sensing and for providing data for angle, SID, data for tracing the receiver 10 outline, and centering information where receiver 10 is positioned behind or underneath the patient. Centering relates to the position of the center of receiver 10 relative to the radiation path or, considered alternatively, the direction of the radiation path relative to the center of receiver 10. Source-to-object distance (SOD), here the distance between the x-ray source and the patient, can also be detected.

The position-sensing signal can be an analog signal or signals or one or more data values, for example. Signals can be from any of a number of types of sensor and sensor-reader apparatus, including inclinometers, radio-frequency devices, electromagnetic coils, and audio signals, for example. Sensors can be located in corners of the grid, holder or the receiver, or may be integrated into the grid, holder or receiver design itself. Whatever sensor configuration is used, the one or more position-sensing signals from sensor apparatus 40 go to a control logic processor 48 that provides the control logic for a display apparatus 50.

Display apparatus 50 is energizable to generate, in response to the position-sensing signals, a display that shows the technician the disposition of receiver 10 relative to radiation path R. In the embodiment shown in FIG. 3B, display apparatus 50 has both a display screen 52 that forms a displayed image to assist alignment and a projector 54 that forms a display by projection, wherein the projected display includes information to assist adjustment by projecting an image to indicate receiver location and related information. Display apparatus 50 may be equipped with either or both projector 54 and display screen 52 devices. In one embodiment, numeric SID and angular orientation values appear only on display screen 52, with centering data displayed using projector 54. Alternately, SID and angular orientation values can be projected onto the patient along with a centering target. It should be noted that display of the actual SID value can be particularly useful for radiographic imaging such as thoracic imaging, since there is an inverse squared relationship between the SID and the amount of radiation that is incident at the receiver. By way of comparison, the SID value is generally not a concern to the operator when obtaining dental and mammographic images, since close distances are used, with positioning and tolerances dictated by the design of existing radiological equipment and by conventional practices used for those types of imaging.

Projector 54 as Display Apparatus 50

Projector 54, shown mounted on the x-ray source 20 in FIG. 3B and following, may be a pico-projector, such as a Pico Projector Display from Microvision Inc., Redmond, Wash., USA, or a Micro Projector from AAXA Technologies, Inc., Santa Ana, Calif., for example. Image forming devices such as these are advantaged for a number of reasons, including small size, low weight, and low power requirements. These small-footprint projectors, currently used in cell-phone and other highly portable electronic devices, scan one or more low-power solid-state light sources, such as light-emitting diodes (LEDs) or lasers onto a display surface. This type of projector requires a small number of optical components for projection over a range of distances. The solid-state light source itself can typically be turned on and off rapidly as needed, so that power is consumed only for those image pixels that are projected. This allows the display device to operate at low power levels, so that battery power could be used for projector 54. Alternate embodiments use other types of electronic imaging projectors as image forming apparatus, such as those that employ a digital micromirror array such as the Digital Light Processor (DLP) from Texas Instruments, Inc.; an array of micro-electromechanical grating light valves, such as the Grating Light Valve (GLV) device from Silicon Light Machines, Inc.; or a liquid crystal device (LCD) including a Liquid Crystal on Silicon (LCOS) device. In an alternate embodiment, projector 54 is provided by a light source and a movable target, with a motor or other actuator that moves the target, where the target is positioned in the path of the light source for providing an image that shows the receiver location.

Figure 4:
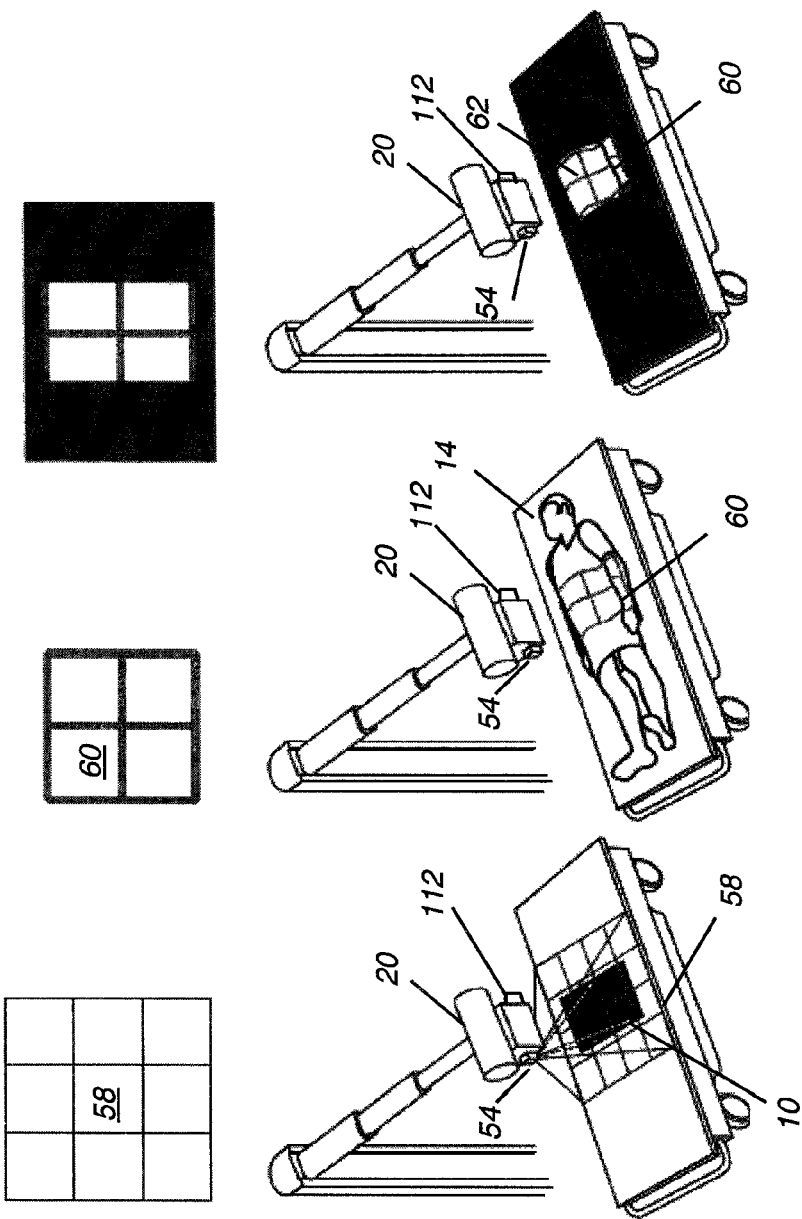
FIG. 4 shows perspective views of a projected image that is used to indicate the relative location of the receiver behind or underneath the patient.

The perspective views of FIG. 4 show how projector 54 performs the display function according to one embodiment of the present invention. Projector 54 can project light to form images over an image field 58 that exceeds the area of receiver 10, as shown at left. When receiver 10 is located using sensor apparatus 40, projector 54 displays a receiver pattern 60 on patient 14, wherein receiver pattern 60 indicates at least an outline showing the location of receiver 10 behind or underneath patient 14. At the right, the desired alignment is shown, wherein a collimator pattern 62, emitted from the collimator light source in the x-ray tube head, is aligned with receiver pattern 60. Notably, with this arrangement, projector 54 can project an image over an area that exceeds the size of receiver 10, enabling the outline of receiver 10 to be displayed prior to centering of the collimator and radiation path onto receiver 10.

Figure 5A:
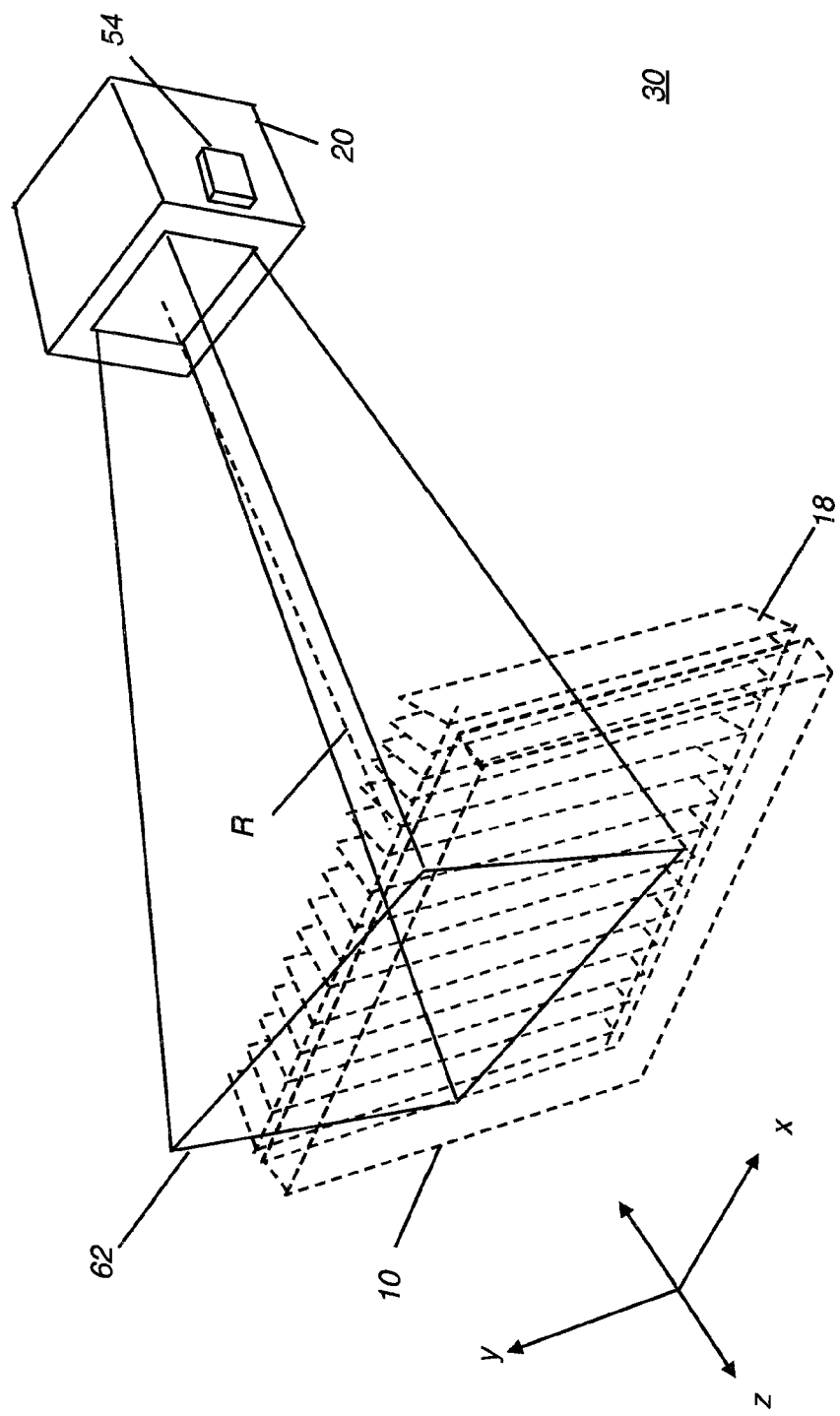
FIG. 5A is a perspective view that shows a collimator pattern displayed from the radiation source, misaligned with the imaging receiver.
Figure 5B:
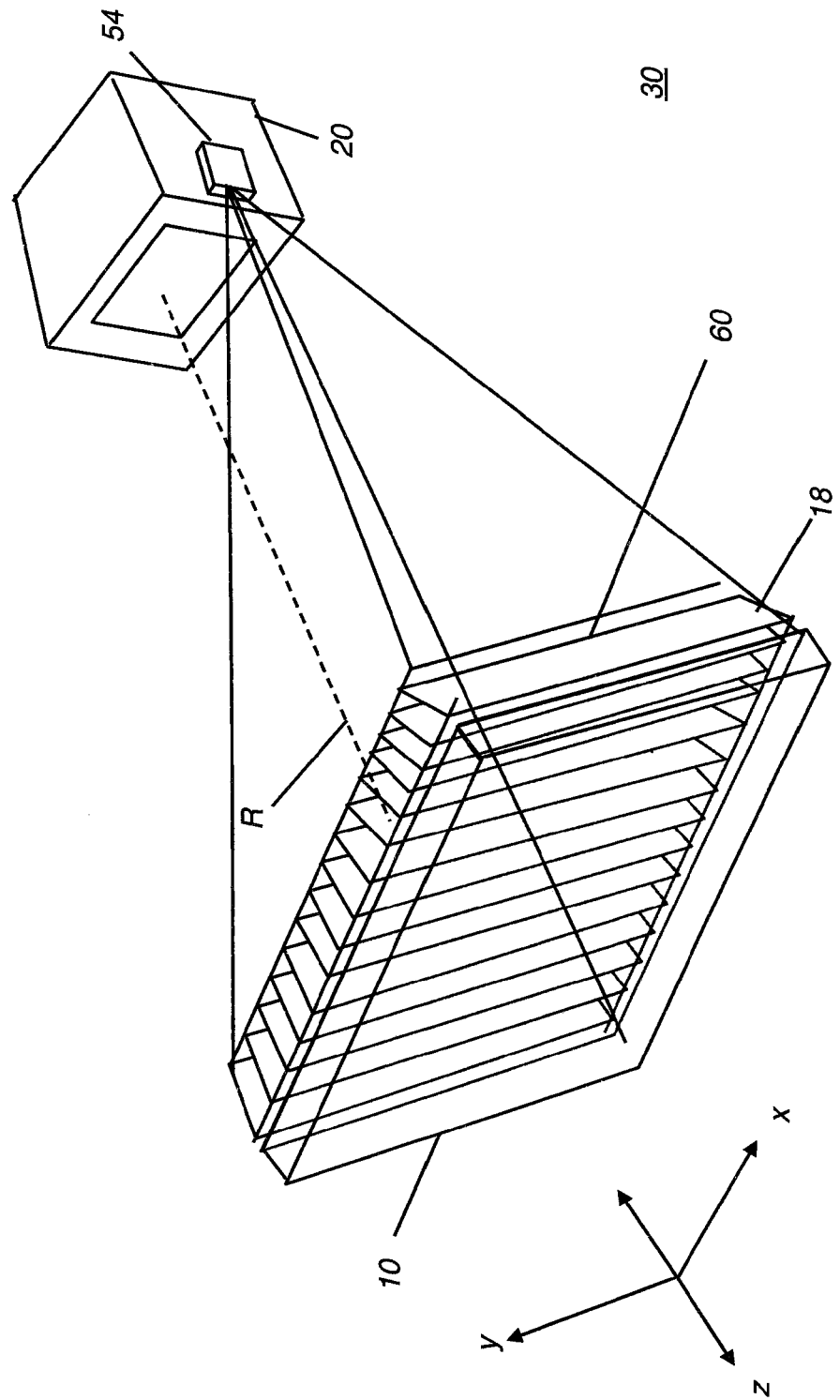
FIG. 5B is a perspective view that shows display of a receiver pattern, also with the radiation source misaligned with the imaging receiver.
Figure 5C:
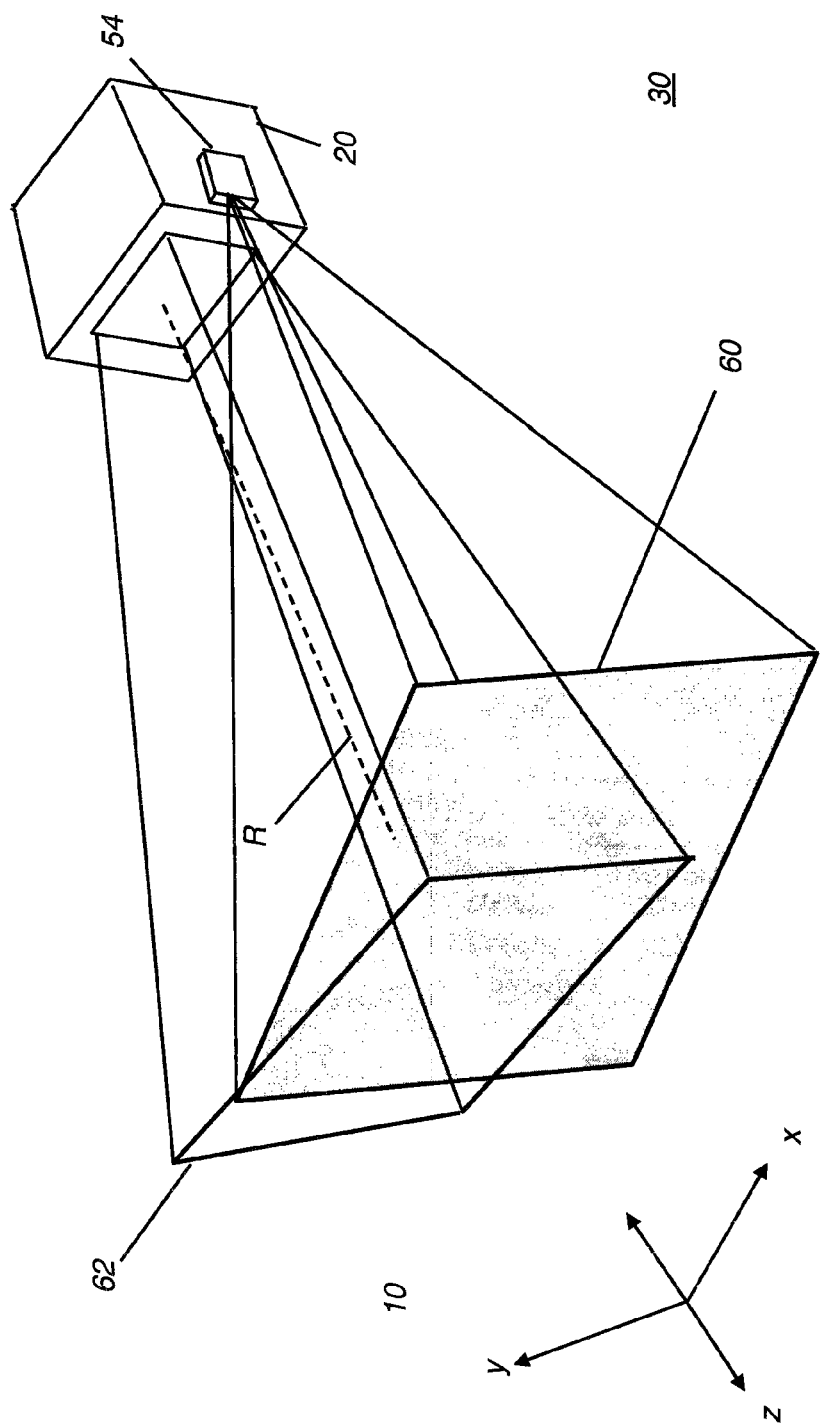
FIG. 5C is a perspective view that shows the overlaid patterns projected from the collimator light and the projector, with the radiation source misaligned with the imaging receiver.
Figure 5D:
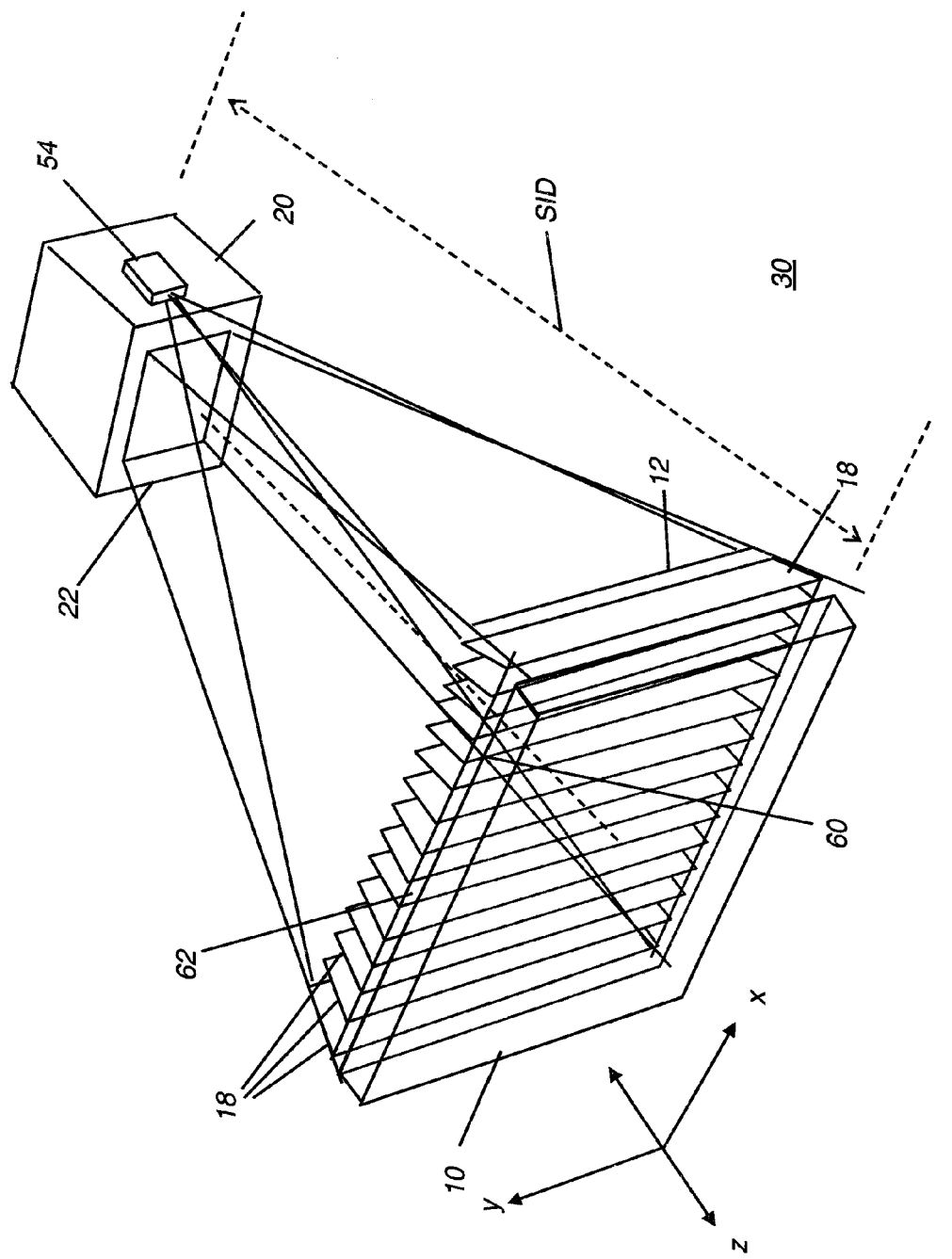
FIG. 5D is a perspective view that shows alignment of the radiation source to the imaging receiver and corresponding alignment of projected patterns.

The perspective view of FIG. 5A shows collimator pattern 62 that is displayed from radiation source 20 in a spatial arrangement wherein the radiation path of radiation source 20 (centered along axis R as described previously) is not aligned with receiver 10 or its grid 12. The perspective view of FIG. 5B shows projector 54 in display apparatus 50, projecting receiver pattern 60 directly at receiver 10. FIG. 5C shows the overlaid paths and mismatched patterns 60 and 62 that indicate poor alignment between radiation source 20 and receiver 10. The perspective view of FIG. 5D then shows correct alignment, wherein receiver pattern 60 and collimator pattern 62 are center-aligned and symmetrical. It can be observed that parallax problems between projector 54 and the collimator pattern 62 can be encountered when the SID is incorrect, with receiver 10 either too far or too near with respect to radiation source 20.

Projector 54 focus can be achieved in a number of ways. Laser projectors do not need focus adjustment. Autofocus apparatus can be used for other projector types, using a range-finding signal such as an ultrasonic signal or infrared (IR) light, for example, to measure the distance from the source to the subject being imaged. FIG. 4 shows an autofocus apparatus 112 that is in signal communication with projector 54 for determining distance to the subject. Autofocus and range-finding methods and devices are inexpensive and well-known to those skilled in the image capture arts. Alternately, information from sensor apparatus 40 can be used to determine the focus distance and used for automatic focusing.

Figure 6:
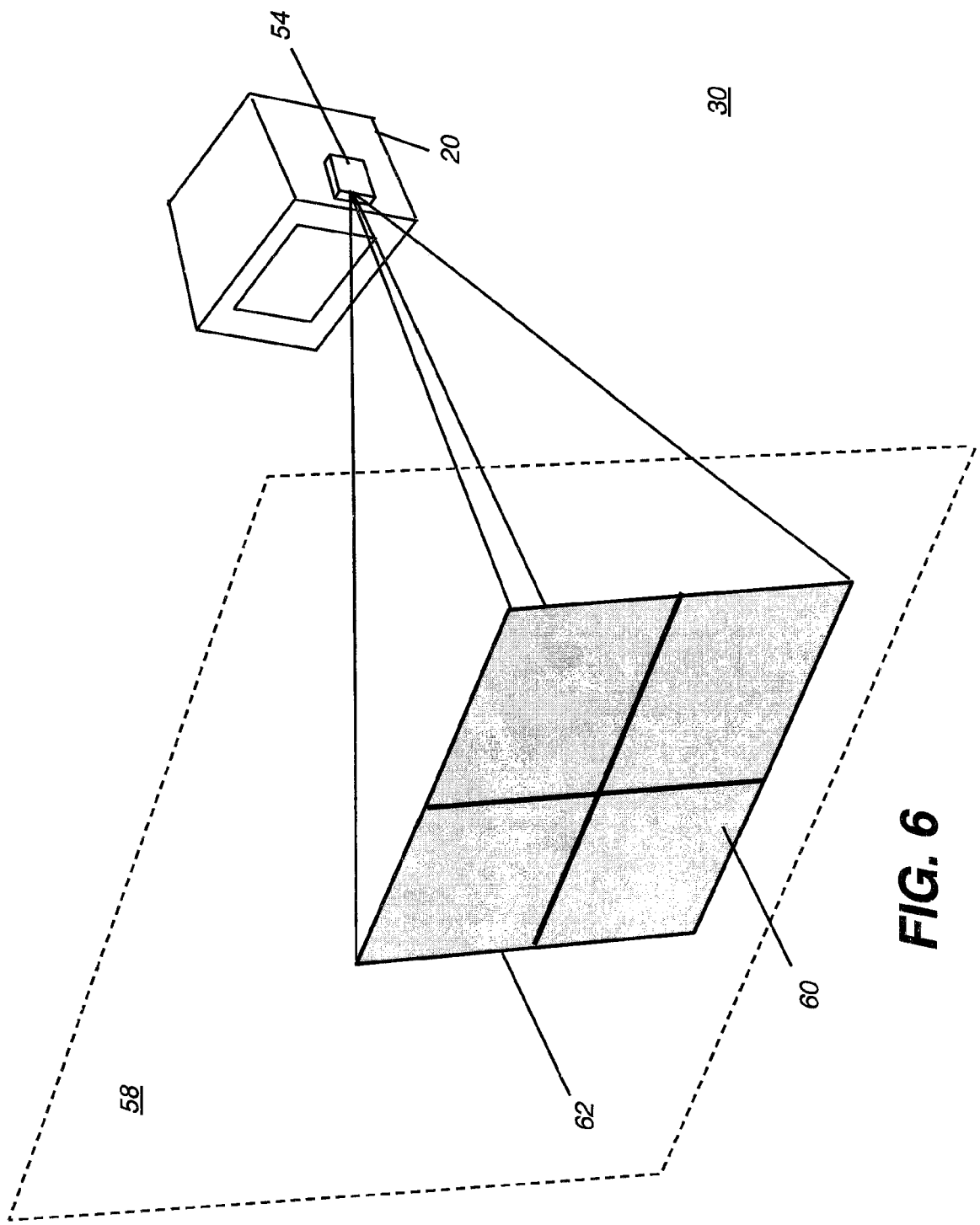
FIG. 6 is a perspective view showing the display of a receiver pattern relative to the full available field for display from the projector.

The perspective view of FIG. 6 shows the projector field 58, having an area that exceeds the size of the projected pattern 60. This capability allows projector 54 to display the needed information for source-to-receiver alignment.

The adjustments needed relate to the spatial relationship between the radiation source 20 and receiver 10 with respect to parameters such as aim centering and angle of the receiver relative to the radiation path, and of source-to-image distance along to the radiation path. Display of the receiver outline is also of value for making collimator adjustments that reduce backscatter.

Figure 7A:
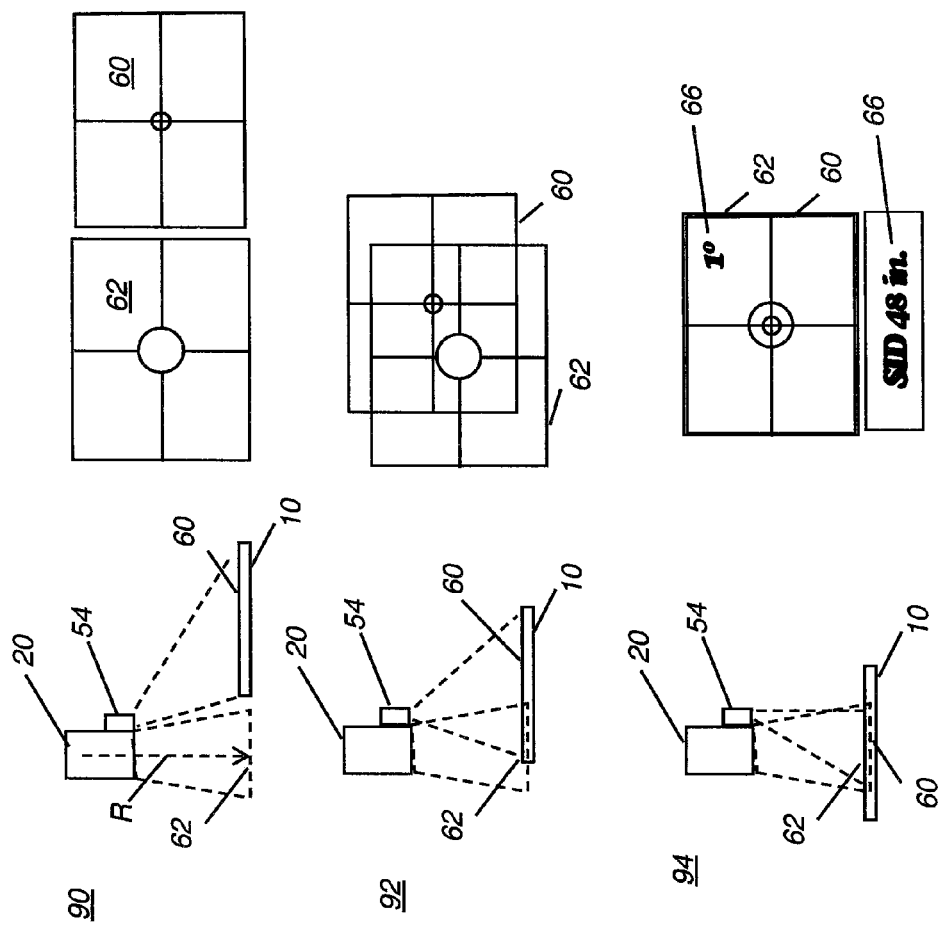
FIGS. 7A and 7B are diagrams that show how projected light patterns align under various conditions, including centering, angular, and distance differences.
Figure 7B:
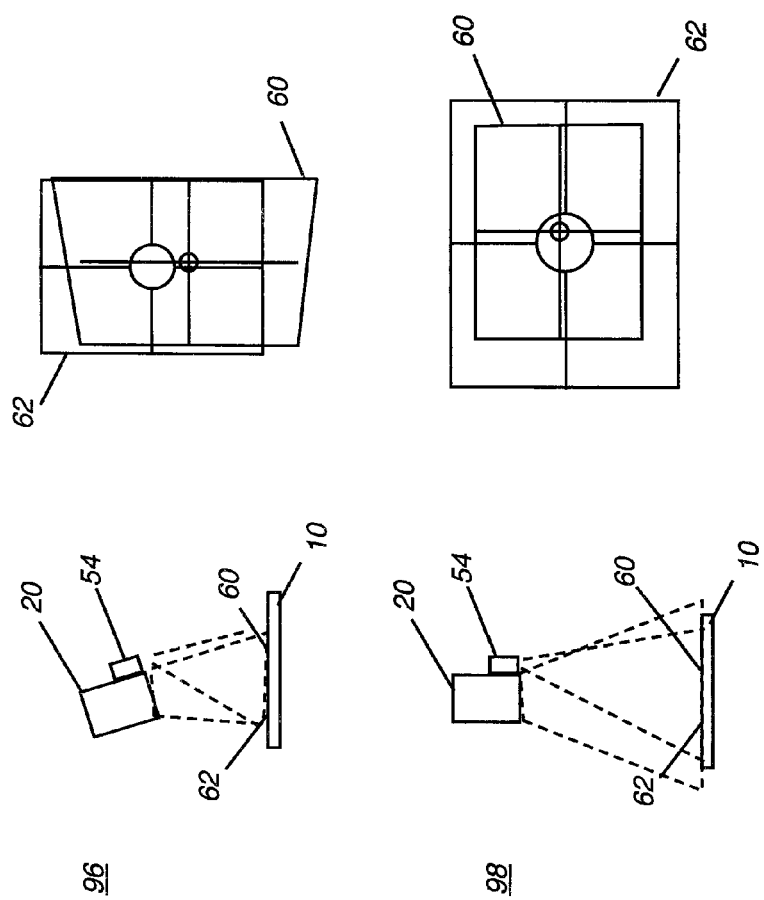

The positional relationship of displayed patterns from projector 54 and from the collimator light of the x-ray tube head can be used as indicators of alignment. By way of example, FIG. 7A shows how alignment of collimator pattern 62 from the collimator light with receiver pattern 60 from projector 54 indicates needed alignment adjustment of radiation source 20 with its receiver 10. The patterns shown at 60 and 62 are representative examples selected for illustration and can take any of a number of forms, including, but not limited to, crosshair patterns, including crosshair patterns with or without a central circle as shown in the example of FIGS. 7A and 7B. At a relative position 90, source 20 and receiver 10 are not aligned and respective patterns 62 and 60 indicate this misalignment. At a relative position 92, source 20 is closer to alignment with receiver 10, closer to centering than shown at position 90, and patterns 62 and 60 display as somewhat overlapping but are not centered with respect to each other. At a relative position 94, source 20 and receiver 10 are aligned and the displayed respective patterns 62 and 60 are overlaid to indicate this centering alignment. In addition, position 94, with both patterns 60 and 62 at the same size and over substantially the same area, also indicates that the collimator has been properly set to limit the radiation distribution and to reduce the likelihood of backscatter. Values 66 for SID and angle are also displayed by projector 54. In an alternate embodiment, a source-to-object distance (SOD) also displays. The projected values can be positioned within or outside receiver pattern 60. In alternate embodiments in which collimator blade position can be sensed, additional information on properly sizing and orienting the collimated light beam can also be provided in the display.

FIG. 7B shows other examples that represent poor relative positioning of source 20 and receiver 10. In a relative position 96, source 20 is nearly centered with respect to receiver 10, but the angle is skewed from normal. Receiver pattern 60 is accordingly non-rectangular, such as having a keystone pattern, for example, indicating the angular relationship of the radiation path from source 20 and receiver 10. In a relative position 98, source 20 is nearly centered with respect to receiver 10, but either the source-to-image distance (SID) is incorrect or, if correct, the collimator should be adjusted to reduce backscatter. In this case, the respective patterns 60 and 62 appear to be of different sizes to indicate the need for SID adjustment.

Where projection is used for display apparatus 50, in addition to the receiver 10 outline, information of various types can be displayed on or alongside the patient, for example:

a) Location of the receiver with a colored light. Using the same sensors that assist with alignment the apparatus can detect and highlight the outline of the imaging receiver.

b) AEC location relative to the patient. Different display representation is used for active and inactive AEC cells. Projection of the AEC location is described in commonly assigned, copending U.S. patent application Ser. No. 13/083,776, filed Apr. 11, 2011, by Michael C. Lalena et al.

c) Grid information, including grid ratio, transverse vs. longitudinal grid orientation.

d) The actual SID and the recommended SID, either by default or provided by system logic, given the type of exam and grid used.

e) Information on Patient, Exam information: Patient Name, Room #, Patient ID, DOB, to confirm that this is the correct patient and the correct exam.

f) A partial subset of the alignment information that is displayed on a display monitor, as described subsequently, projected onto the patient.

Display Screen 52 as Display Apparatus 50

Figure 8:
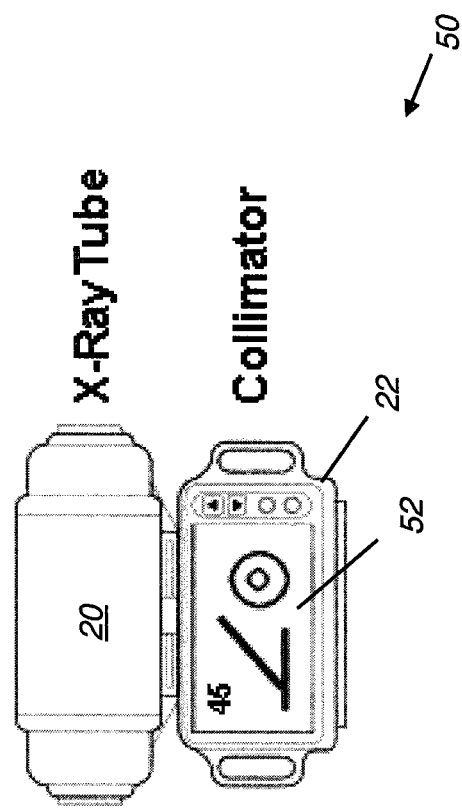
FIG. 8 is a plan view that shows the use of a display screen coupled to the collimator for displaying information indicative of the spatial relation between the radiation source and its receiver.

FIG. 8 shows display screen 52 that can supplement or substitute for projector 54 in an alternate embodiment of display apparatus 50. In one embodiment, display screen 52 is mounted near collimator 22 as shown, so that the operator can view displayed results while moving radiation source 20 into position. In alternate embodiments, the alignment utility may be provided on a removable or remote display screen or on display 610 (FIG. 1), the display console that is part of radiographic imaging apparatus 30 itself.

Figure 9A:
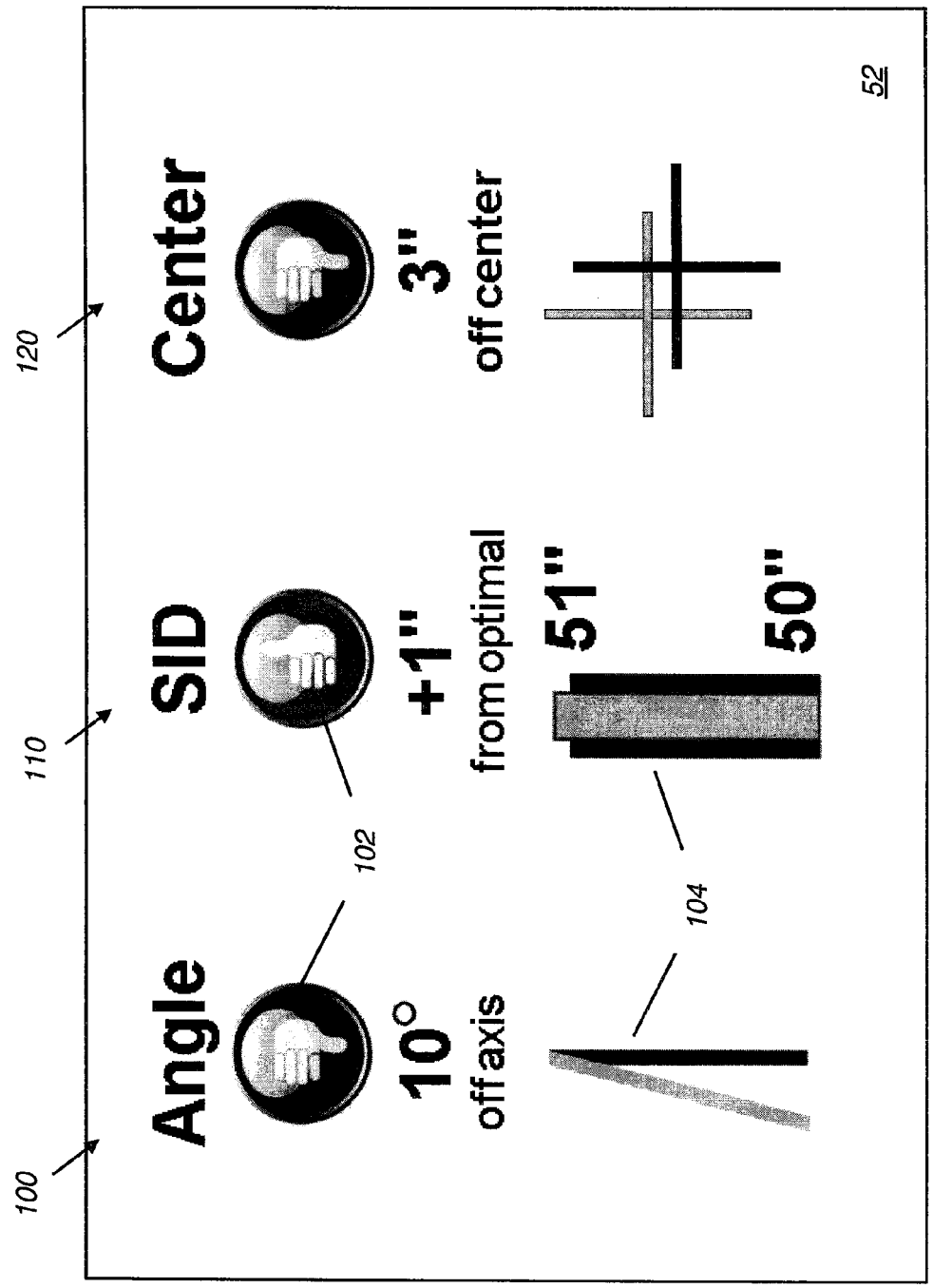
FIGS. 9A, 9B, and 9C show operator interface examples for use of a display screen as a display apparatus.
Figure 9B:
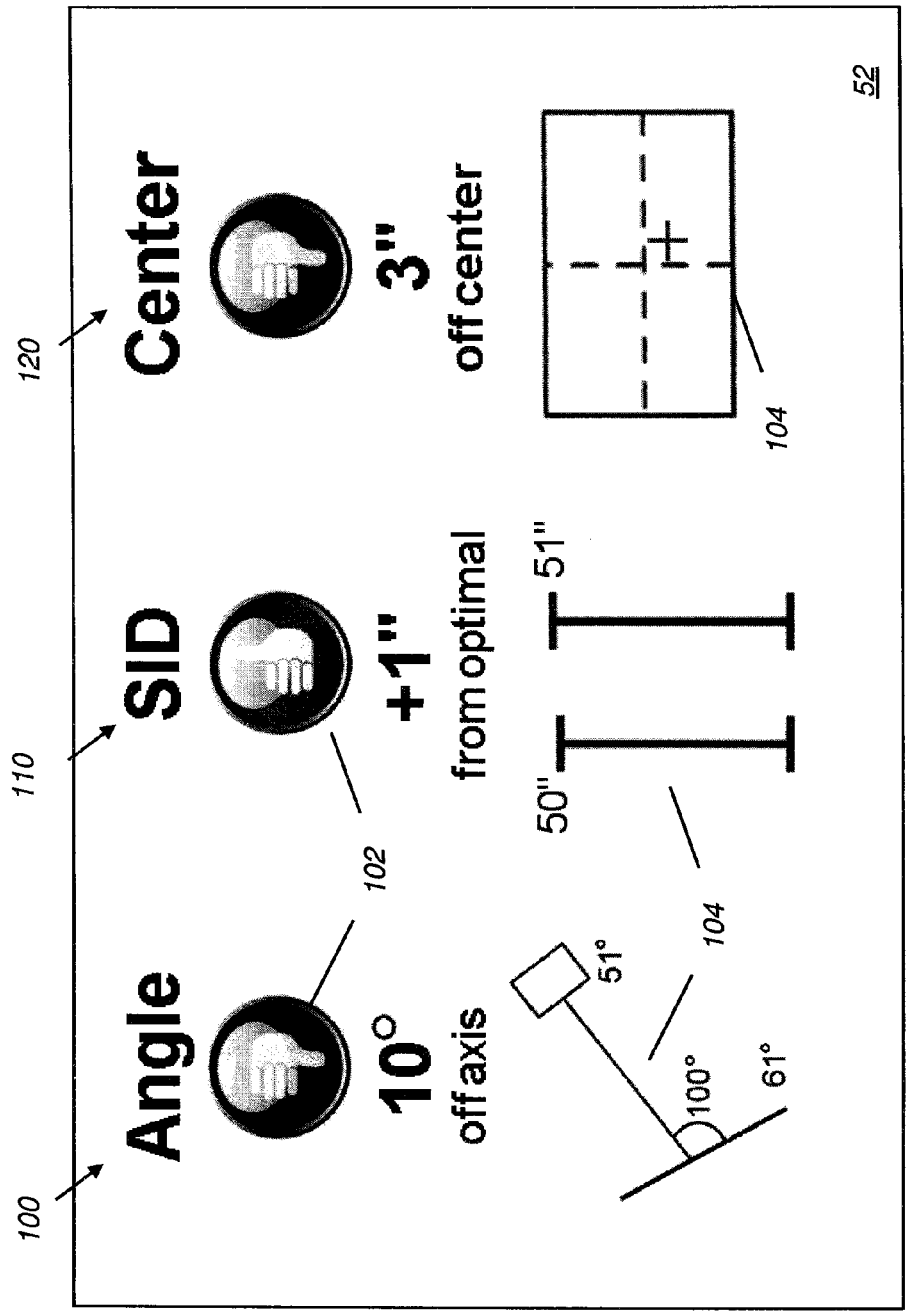
Figure 9C:
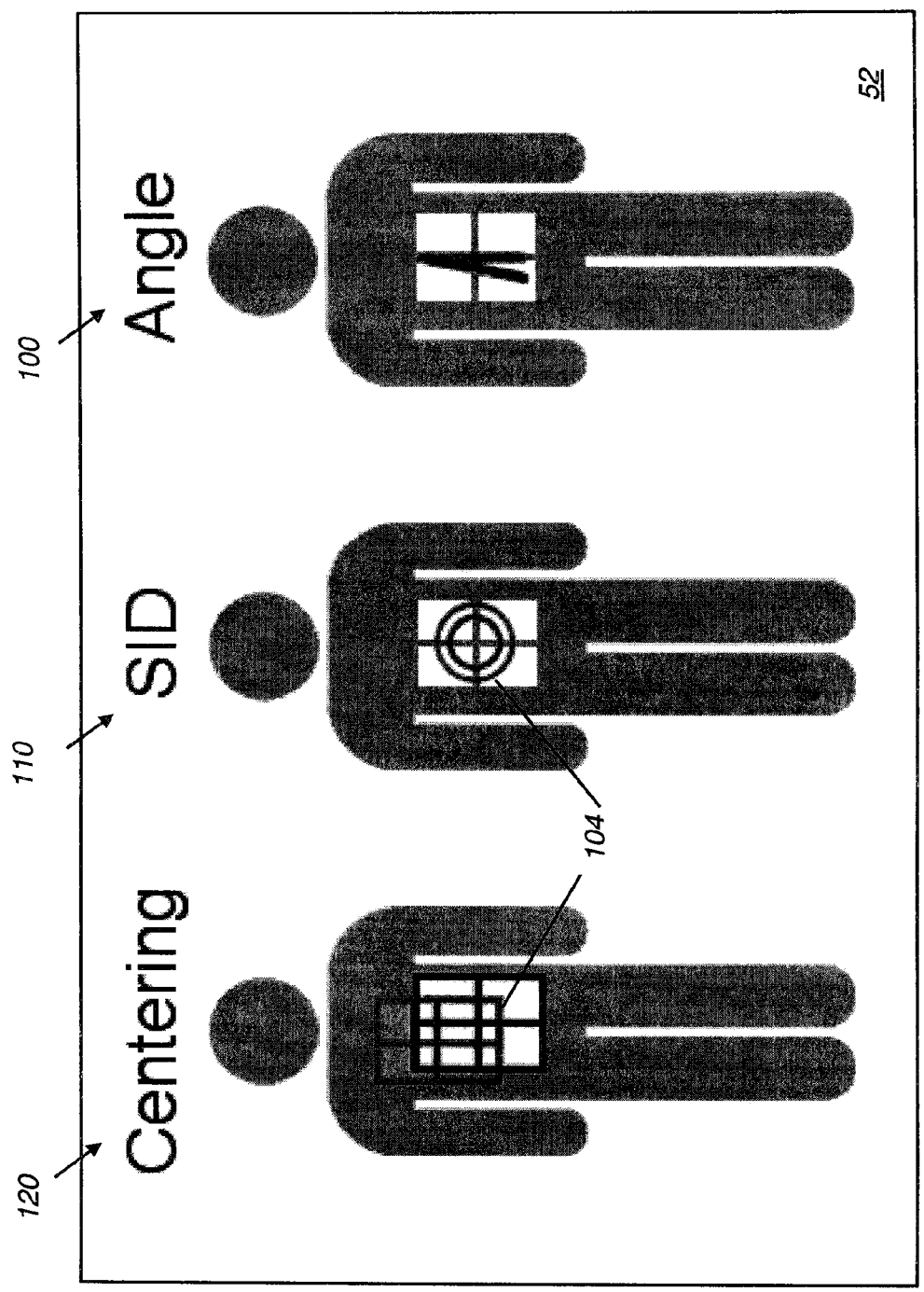

FIGS. 9A, 9B, and 9C show operator interface examples when using display screen 52 as display apparatus 50. Various graphical icons and images are used to symbolize the adjustments needed for proper centering, angulation, and SID. An angle adjust indicator 100 provides various graphical and measured data to help guide proper angular adjustment of the source 20 to receiver 10. Angular information displays one or more of the following:

(i) Receiver angle. An angular measurement relative to true horizontal can be obtained from the optional inclinometer 28 (FIG. 3B) or from other sensor apparatus 40 data.

(ii) Tube angle for radiation source 20. This angular measurement relative to true horizontal can similarly be calculated from inclinometer 28 or other sensor apparatus 40 data.

(iii) Receiver/grid to source 20 angle. This relative angular measurement between receiver 10 and source 20 can be obtained using measurements from one or more optional inclinometers 28 (FIG. 3B) or from other sensor apparatus 40 data.

(iv) Intercept angle data for source-to-grid 12 alignment.

(v) Source to receiver angle relative to desired angle, calculated from sensor apparatus 40 measurements. This includes adjustment for non-normal angles.

A SID indicator 110 lists not only the current SID value obtained from measured data, but, in the embodiment shown, also shows the amount of adjustment needed. A centering indicator 120 provides text and graphical information on centering error and needed adjustment direction. In FIG. 9B, centering indicator 120 includes a graphic element 104 that shows the portrait/landscape orientation of the receiver. Icons 102 use color, animation, including flashing or video clips, and symbols of different types to indicate the needed adjustment direction for the corresponding value. Graphic elements 104 are also provided to help visually indicate the adjustment needed. Graphic elements 104 can be any of a number of types of suitable element, including circles, bars, or other shapes. Color can be used to indicate correct angular, centering, or distance values, with differences in color indicating the recommended direction of needed change, if any, and color transitions indicating movement between positions. Various thresholds are used to determine how close an adjustment is to a desired setting.

Figure 10:
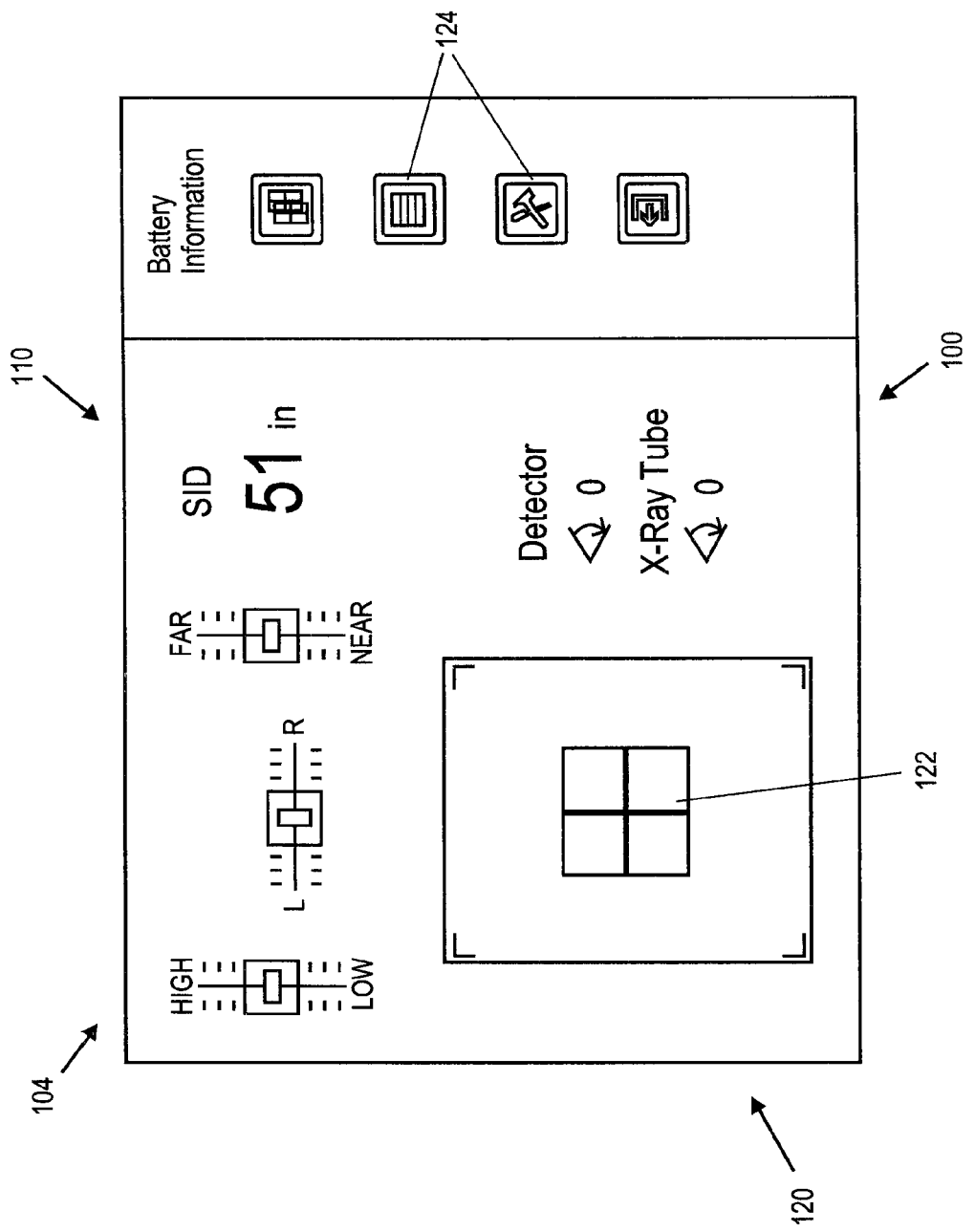
FIG. 10 shows an operator interface arrangement for the display screen in an alternate embodiment.

FIG. 10 shows a plan view of an alternate embodiment for the operator interface on display screen 52. SID indicator 110 lists the current SID value obtained from measured data. Here, graphic elements 104 include sliders that show the relative amount of adjustment that is needed for centering, distance, and angle. Centering of the slider indicates correct positioning. Angle adjust indicator 100 shows the measured angular values for the receiver or x-ray source relative to true horizontal or, optionally, relative to each other or to a preferred setting. In an optional embodiment, the difference between their relative angles is displayed. Centering indicator 120 shows an image or outline of receiver 10, such as at portrait or landscape orientation, with a superimposed icon 122 that shows the relative position and shape of the x-ray beam. Control buttons 124 provide useful utilities for improving alignment, obtaining information about the system or about system components, and other functions. In an alternate embodiment, one of the control buttons 124 is used to set up the view type for the upcoming radiographic image (such as, for example, an AP chest exam view type) and to indicate the type of grid used, if any. This setup can then cause specific SID and angle values to be assigned and displayed for the image.

FIG. 11 shows a sequence of operator interface display screens for a display screen 52 that is mounted near collimator 22 and that changes orientation as radiation source 20 angle changes. At a position 130, a receiver icon 132 displays, along with a centering target icon 134 and a radiation source icon 136. At a position 140, centering is partially achieved, but the radiation source 20 must be redirected toward the receiver. At a position 150, radiation source 20 is being turned and the screen display dynamically re-orients itself to represent positions of components with receiver icon 132 and icons 134 and 136. A SID icon 152 graphically shows that radiation source distance to the receiver must be adjusted. SID icon 152 changes position as the SID changes. At a position 160, proper centering, angle, and SID are obtained. The SID value displays as shown at SID indicator 110.

In an embodiment of the present invention, display apparatus 50 provides considerable information relative to the position of the x-ray source and receiver, as well as other types of information that may be relevant to the imaging session. This may include date, time, temperature or other environmental conditions, information about the radiography unit itself, such as identification number, serial number, or manufacturer and model identification. In one embodiment, instructions, recommendations, or warning information are also provided to assist the operator in making needed adjustments or obtaining the image, including information on what type of image has been ordered and suggested setup and exposure values. Detector information can also be displayed. Patient identifying data can be listed, including name, age or date of birth, patient number, room number, information on measured values or patient blood type, and the like.

For embodiments using optional display screen 52, the capability for editing or input by the operator may also be provided, including entry or editing of desired exposure setup values, such as generator values, including kVp, mA, mAs, time, ECF, focal spot, collimator settings, AEC setting, grid type recommended or used, and detector type. A worklist that provides a job listing of images and views requested from this patient is also displayed in one embodiment. In one embodiment, display screen 52 also shows acquired images for the patient and allows editing or annotation by the technician for those images.

Values displayed on display screen 52 include relevant alignment information, such as any or all of the following, displayed in symbolic, icon, or text form:

(i) SID or other distance value, such as shortest distance from the x-ray tube to the grid;

(ii) Receiver angle, relative to horizontal or relative to the radiation path;

(iii) X-ray source angle;

(iv) Actual grid angle relative to the actual X-ray source angle; and (v) Actual grid or source angle relative to a desired angle;

In one embodiment, sensors are also able to indicate whether or not grid 12 is used and, if so, the type of grid 12 that is being used. The system can then display the following information on display screen 52 or projected onto the patient:

(i) Transverse or Longitudinal grid type;

(ii) Grid ratio. For example: 6:1, 8:1, 10:1.

(iii) Optimal SID (or SID range) for the grid being used; and (iv) Indication or message to use the correct grid type (transversal or longitudinal) based on detected rotation of the receiver. If the patient is not lying flat, the system can determine this through the grid's inclinometer data, and can also determine this condition using other sensor data.

(v) Warning message related to grid cutoff, a condition that occurs when the angle of the radiation path is excessively skewed to one side or the other of the grid, causing the grid elements to block a substantial amount of radiation.

When the presence/absence of a grid is determined, system logic can automatically select the correct view for the exam or change the existing view to a different one. For example, the system can switch from a non-grid view to a grid view. This new view may have a different name, different exposure parameters or techniques, and different image processing parameters.

In an alternate embodiment of the present invention, the image type or view is determined and one or more appropriate settings for centering, angle, and SID are automatically assigned based on the view type. The view can be set up by the operator, such as using display screen 52 and may specify the type of grid used. Alternately, the view can be determined from measured data, such as inclinometer readings, for example. Thus, for example, with respect to FIG. 3B, an inclinometer 28 reading can indicate a supine view and a sensor apparatus 40 reading can indicate the detection of a specific grid type. This information is then used by control logic processor 48 to determine and display a suitable SID value. As another example, detection of receiver 10 in an upright position indicates that a longer SID can be used for a given grid type. Different SID values and technique settings can be used for different types of chest x-rays, for example, based on this information. Optionally, an instruction on view type can be entered by the operator or technician and appropriate predetermined values for the source-to-image distance or the angle or both can be displayed or used to condition the displayed values according to the operator instruction.

As has been noted previously, there have been other solutions proposed for indicating the location of the imaging receiver relative to the radiation path in order to allow improved alignment. These earlier solutions, however, have not addressed particular problems of tube-to-grid alignment, and of providing numeric values that indicate relative angle for the receiver and source and source-to-image distance. Moreover, earlier solutions do not provide the technician with the needed information for adapting setup and alignment for different grid configurations and for imaging at particular angles other than normal. The apparatus and methods of the present invention provide this information, allowing the technician to set up each exposure under known parameters.

Various information detected by sensor apparatus 40 may also be stored and provided as part of the DICOM (Digital Imaging and Communications in Medicine) header information that is stored with the image data.

Figure 12A:
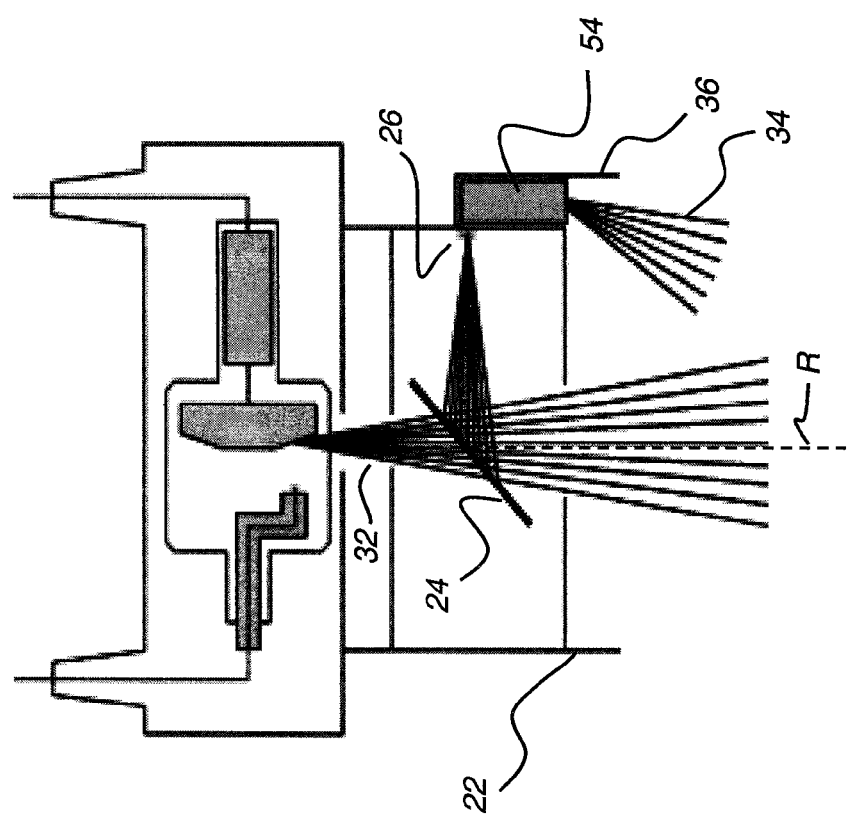
FIG. 12A is a schematic view showing coupling of a projector to the collimator according to one embodiment of the present invention.

Projector 54 can be coupled to collimator 22 in a number of ways. Referring to FIG. 12A, there is shown an embodiment in which a housing 36 that holds projector 54 mounts along an edge of collimator 22. A collimator light 26, typically a light emitting diode (LED) or other solid-state light source, mounts inside collimator 22. A mirror 24, essentially transparent to x-rays, combines the light path from collimator light 26 with the radiation path R of an x-ray beam 32. Projector light 34 can project over a broad angular range, but there can be slight parallax error because its light path is spaced apart from radiation path R.

Figure 12B:
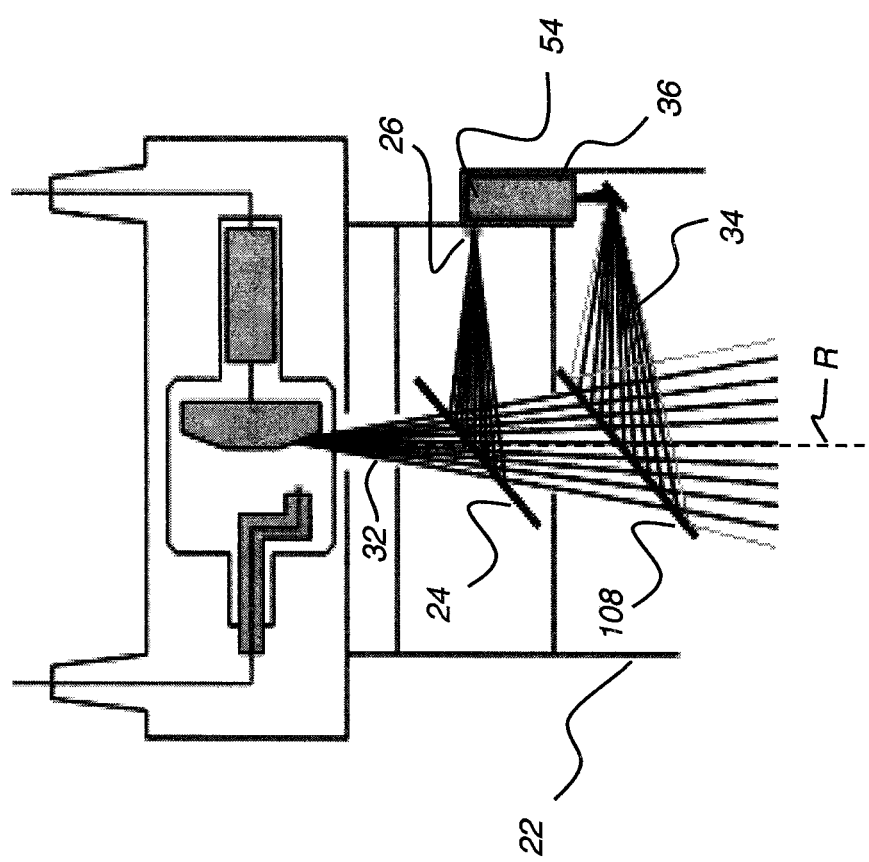
FIG. 12B is a schematic view showing an alternate method for coupling the projector to the collimator.

The alternate arrangement of FIG. 12B uses a second mirror, two-way mirror 108, to align the path of projector light 34 with radiation path R, eliminating the parallax error condition. This arrangement allows projector 54 to project light over a broad angular range.

Figure 12C:
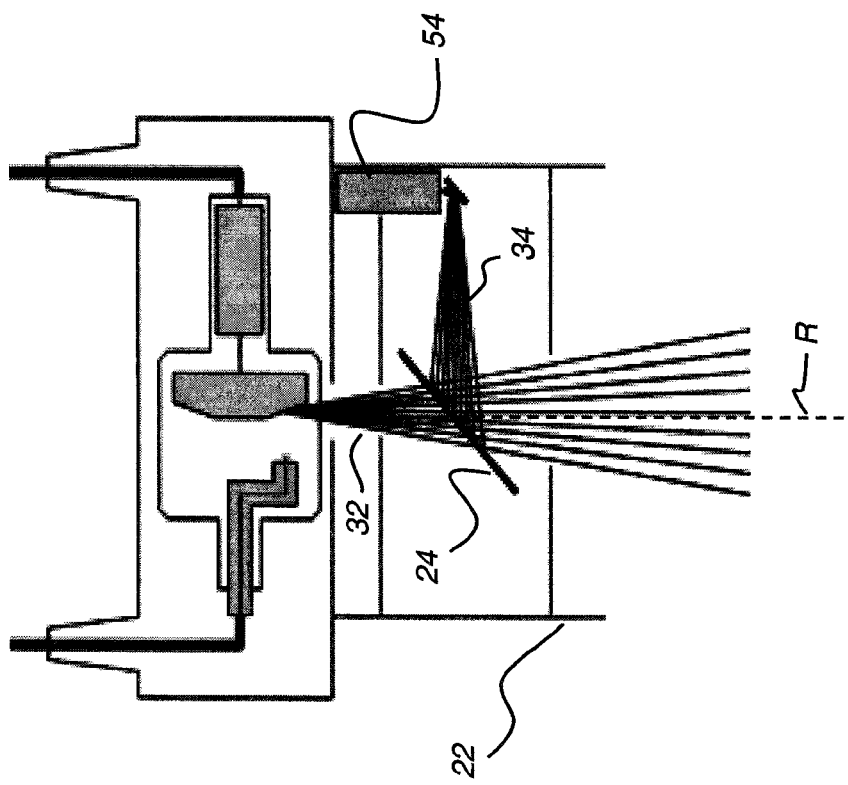
FIG. 12C is a schematic view showing another alternate method for coupling the projector to the collimator.

The alternate arrangement of FIG. 12C replaces the existing collimator light with projector 54. Here, projector 54 is aligned with radiation path R and is capable of performing a number of functions for showing centering information relative to radiation path R. The angular range of projection is more restricted than with the FIG. 12B embodiment, but both the collimation path and receiver location can be shown within a range of angles.

According to one embodiment of the present invention, there is provided a radiography system for obtaining a radiographic image of a subject, the system comprising a radiation source energizable to direct radiant energy along a radiation path; an imaging receiver sensitive to the radiant energy for forming the radiographic image; a sensor apparatus that is disposed to provide one or more output signals that are indicative at least of the outline of the imaging receiver; and a display apparatus that generates, either by projection or on a display monitor, at least the outline of the imaging receiver, in response to the one or more output signals.

According to an alternate embodiment of the present invention, there is provided a radiography system for obtaining a radiographic image of a subject, the system comprising a radiation source energizable to direct radiant energy along a radiation path; an imaging receiver sensitive to the radiant energy for forming the radiographic image; a sensor apparatus that is disposed to provide one or more output signals that are indicative at least of an angle of the receiver relative to the radiation path, and of a source-to-image distance along the radiation path; and a display apparatus that generates, in response to the one or more output signals, a display that provides one or more values indicative of at least the source-to-image distance and the angle of the receiver relative to the radiation path. The display may use either a projector or a display screen or some combination of projector and display devices. Where collimator blade position information is available, the display can also indicate alignment of the boundaries of the radiation along the radiation path to the detector outline.

The invention has been described in detail with particular reference to a presently preferred embodiment, but it will be understood that variations and modifications can be effected within the spirit and scope of the invention. For example, audible feedback tones could be used to supplement display functions for obtaining the needed adjustments for alignment. The presently disclosed embodiments are therefore considered in all respects to be illustrative and not restrictive. The scope of the invention is indicated by the appended claims, and all changes that come within the meaning and range of equivalents thereof are intended to be embraced therein.

PARTS LIST

10. Receiver
12. Grid
14. Patient
18. Plate
20, 20', 20". Radiation source
22. Collimator
24. Mirror
26. Collimator light
28. Inclinometer
30. Radiographic imaging apparatus
32. X-ray beam
34. Projector light
36. Housing
40. Sensor apparatus
42. Coil
44. Sensor element
46. Holder
48. Control logic processor
50. Display apparatus
52. Display screen
54. Projector
58. Field
60. Receiver pattern
62. Collimator pattern
64. Column
66. Value
70. Boom apparatus
90, 92, 94, 96, 98. Relative position
100. Angle adjust indicator
102. Icon
104. Graphic element
108. Mirror 110. SID indicator
112. Autofocus apparatus
120. Centering indicator
122. Icon
124. Control button
130. Position
132. Receiver icon
134. Target icon
136. Radiation source icon
140. Position
150. Position
152. SID icon
160. Position
600. Mobile radiography unit
610. Display
612. Control panel
615. Wheel
620. Frame
625. Handle grip
635. Support member
640. X-ray source
L. Focal line
R. Radiation path

What is claimed is:

1. A mobile radiography system for obtaining a radiographic image of a subject, the system comprising:
   a portable transport frame;
   a sectioned vertical column mounted on the frame and defining a vertical axis and comprising a base section having a fixed vertical position relative to the vertical axis and at least one movable section that is translatable to a variable vertical position along the vertical axis;
   a boom apparatus that supports a radiation source and extends outward from the movable section and has an adjustable height relative to the vertical axis for positioning the radiation source;
   a radiation source energizable to direct radiant energy along a radiation path;
   an imaging receiver sensitive to the radiant energy for forming the radiographic image;
   a sensor apparatus that is disposed to provide one or more output signals that are indicative at least of centering of the radiation path with respect to the receiver, of an angle of the receiver relative to the radiation path, and of a source-to-image distance along the radiation path; and
   a display apparatus that generates, in response to the one or more output signals, a display that shows the centering of the radiation path with respect to the imaging receiver and one or more values indicative of at least the source-to-image distance and one or more values indicative of at least the angle of an imaging plane of the imaging receiver relative to a portion of the radiation path.

2. The radiography system of claim 1 wherein the display apparatus further indicates an outline of the imaging receiver.

3. The radiography system of claim 1 wherein the display apparatus further provides a value indicative of a source-to-object distance or a combination of the source-to-image distance and the source-to-object distance, wherein the display is modified based on a representation of the source-to-object distance.

4. The radiography system of claim 1 wherein the imaging receiver is taken from the group consisting of a film cassette, a computed radiography cassette, and a digital radiography cassette.

5. The radiography system of claim 1 wherein the sensor apparatus senses an electromagnetic signal or field.

6. The radiography system of claim 1 wherein the sensor apparatus comprises an inclinometer.

7. The radiography system of claim 1 wherein the display apparatus comprises a projector that is coupled to the radiation source.

8. The radiography system of claim 1 wherein the display apparatus comprises a display monitor, wherein the display monitor is disposed along the boom apparatus that supports the radiation source, wherein the display monitor comprises a touch screen monitor.

9. The radiography system of claim 1 wherein the sensor apparatus is part of the receiver or wherein the sensor apparatus is part of a holder that is coupled to the receiver.

10. The radiography system of claim 1 wherein the one or more output signals from the sensor apparatus further provide information about a grid type used with the imaging receiver, where the display is configured to show said one or more values using information about the grid type.

11. The radiography system of claim 1,
    where the display apparatus shows one or more numeric values indicative of the current source-to-image distance, one or more numeric values indicative of a user selectable source-to-image distance, one or more numeric values indicative of the angle of the imaging plane of the receiver, and one or more numeric values indicative of the angle of the radiation path.

12. A method for obtaining a radiographic image of a subject comprising:
    obtaining one or more signals indicative of centering of an imaging receiver with respect to a radiation path from a radiation source, of an angle of an imaging plane of the receiver, of an angle of the radiation path, and of a current source-to-image distance along the radiation path; and
    generating, in response to the one or more obtained signals, a display that shows at least the centering of the imaging receiver relative to the radiation path and displaying a first value indicative of the current source-to-image distance, a second value indicative of a user selectable source-to-image distance, a third value indicative of the angle of the imaging plane of the receiver, and a fourth value indicative of the angle of the radiation path.

13. The method of claim 12 wherein generating the display comprises forming a display on a display screen.

14. The method of claim 12 wherein generating the display comprises projecting an image toward the subject, the image including the centering of the imaging receiver with respect to the radiation path and that provides one or more values indicative of at least the source-to-image distance and the angle of the imaging receiver relative to the radiation path.

15. The method of claim 12 wherein obtaining the one of more signals further comprises obtaining a signal indicating a grid type and wherein displaying one or more values comprises using information about the grid type.

16. The method of claim 12 further comprising storing information obtained from the one or more signals with the image data.

17. The method of claim 12 further comprising obtaining an operator instruction that specifies a view type and displaying a predetermined value indicative of the source-to-image distance or the angle or both according to the view type.

18. The method of claim 12 wherein obtaining the one or more signals further comprises obtaining a signal used for focus of a projector that is coupled to a collimator of the radiation source.

19. The method of claim 12 further comprising re-orienting the display according to the angular orientation of the radiation source relative to the receiver.

20. A method for obtaining a radiographic image of a subject comprising:
- obtaining one or more signals indicative of centering of an imaging receiver with respect to a radiation path from a radiation source, of an angle of the receiver relative to the radiation path, and of a source-to-image distance along the radiation path; and
- generating, in response to the one or more obtained signals, a display that shows at least the centering of the imaging receiver relative to the radiation path and displaying one or more values indicative of the source-to-image distance or the angle or both,
- wherein generating the display comprises projecting an image toward the subject, the image including the centering of the imaging receiver with respect to the radiation path and that provides one or more values indicative of at least the source-to-image distance and the angle of the imaging receiver relative to the radiation path.

* * * * *